US008940498B2

(12) United States Patent
Sato et al.

(10) Patent No.: US 8,940,498 B2
(45) Date of Patent: Jan. 27, 2015

(54) BIOLOGICAL ASSAYS FOR THE CHARACTERIZATION OF CELLS USING SINGLE-CELL TRACKING AND USES THEREOF

(71) Applicants: Masahiko Sato, Quebec (CA); Sachiko Sato, Quebec (CA)

(72) Inventors: Masahiko Sato, Quebec (CA); Sachiko Sato, Quebec (CA)

(*) Notice: Subject to any disclaimer, the term of this patent is extended or adjusted under 35 U.S.C. 154(b) by 13 days.

(21) Appl. No.: 13/867,270

(22) Filed: Apr. 22, 2013

(65) Prior Publication Data

US 2013/0288293 A1      Oct. 31, 2013

Related U.S. Application Data

(60) Provisional application No. 61/640,121, filed on Apr. 30, 2012.

(51) Int. Cl.
   *C12Q 1/02*          (2006.01)

(52) U.S. Cl.
   USPC .............................................. 435/29

(58) Field of Classification Search
   USPC .................................... 435/29, 7.23
   See application file for complete search history.

(56) References Cited

U.S. PATENT DOCUMENTS

| 4,256,832 | A | * | 3/1981 | Findl et al. | 435/6.14 |
|---|---|---|---|---|---|
| 5,326,691 | A | * | 7/1994 | Hozier | 435/6.15 |
| 5,925,524 | A | * | 7/1999 | Kowalski | 435/6.16 |
| 2009/0304575 | A1 | * | 12/2009 | Lacal Sanjuan et al. | 424/1.11 |
| 2013/0217061 | A1 | * | 8/2013 | Sato et al. | 435/29 |

FOREIGN PATENT DOCUMENTS

| CA | PCT/CA2007/001685 A1 | 3/2008 |
|---|---|---|
| CA | PCT/US2010/046343 A1 | 3/2011 |

OTHER PUBLICATIONS

Freire P. et al. Cytotoxic Effects in Mammalian Vero Cells Exposed to Pentachlorophenol. Toxicology 210:37-44, 2005.*
Ekwall B. Screening of Toxic Compounds in Tissue Culture. Toxicology 17(2)127-142, 1980.*
Reuben, Reducing Environmental Cancer Risk: What We Can Do Now, the President's Cancer Panel Annual Report, 2010, 2008-2009 Annual Report, 1-208, The President's Cancer Panel, United States.
International Agency for Research on Cancer, Agents Classified by the IARC Monographs, vols. 1-107, http://monographs.iarc.fr/ENG/ Classification/, 2013, 1-33, International Agency for Research on Cancer, France.
Hartung, Toxicology for the twenty-first century, Nature, 2009, 208-212, vol. 460, Macmillan, New York.
Kirkland et al, Evaluation of the ability of a battery of three in vitro genotoxicity tests to discriminate rodent carcinogens and non-carcinogens I. Sensitivity, specificity and relative predictivity, Mutation Research, 2006, 29-42, vol. 584, Elsevier, United States.
Tennant et al, Prediction of chemical carcinogeenicity in rodents from in vitro genetic toxicity assays, Science, 1987, 933-941, vol. 236, AAAS, United States.
Weinberg, The Nature of Cancer, The Biology of Cancer, 2007, 25-56, Garland Science, New York.
Errington et al, Time-lapse microscopy approaches to track cell cycle progression at the single-cell level, Current Protocols in Cytometry, 2005, Unit 12.4, Supplement 31, John Wiley & Sons, Inc., Hoboken.
Al-Kofahi et al, Automated cell lineage construction: a rapid method to analyze clonal development established with murine neural progenitor cells, Cell Cycle, 2006, 327-335, 5:3, Landes Bioscience, Austin.
Khan et al, ProgeniDB: a novel cell lineage database for generation associated phenotypic behavior in cell-based assays, Cell Cycle, 2007, 868-874, 6:7, Landes Bioscience, Austin.
Davis et al, The large-scale digital cell analysis system: an open system for nonperturbing live cell imaging, Journal of Microscopy, 2007, 296-308, vol. 228 pt. 3, The Royal Microscopical Society, Oxford.
Knight et al, Live cell imaging using confocal microscopy induces intracellular calcium transients and cell death, American Journal of Physiology Cell Physiology, 2003, C1083-C1089, vol. 284, The American Physiological Society, Bethesda.
Liu et al, Cell contour tracking and data synchronization for real-time, high-accuracy micropipette aspiration, IEEE Transactions on Automation Science and Engineering, 2009, 536-543, vol. 6 No. 3, IEEE Robotics and Automation Society, United States.
Wang et al, An Automated Micropositioning System for Investigaging *C. Elegans* Locomotive Behavior, The Journal of Laboratory Automation, 2009, 269-276, 14(5), Society for Laboratory Automation, United States.
Lu et al, Single Cell Deposition and Patterning with a Robotic System, Plos One, 2010, e13542, vol. 5 issue 10, Plos, United States.
Wong et al, Non-invasive imaging of human embryos before embryonic genome activiation predicts development to the blastocyst stage, Nature Biotechnology, 2010, 1115-1121, vol. 28 No. 10, Nature Publishing Group, New York.

(Continued)

*Primary Examiner* — Ralph Gitomer
(74) *Attorney, Agent, or Firm* — Richards Patent Law P.C.

(57) ABSTRACT

The invention relates to the field of medicine. More particularly, described herein are biological markers associated with phenotypical and/or genotypical alterations in a cell and to methods for assessing mammalian cells. Also described are methods for assessing the condition of a population of cells, methods for assessing carcinogenicity of compounds and methods for quantitatively determine the quality of cell populations.

9 Claims, 8 Drawing Sheets

(56) References Cited

OTHER PUBLICATIONS

Lu et al, Robotic ICSI (intracytoplasmic sperm injection), IEEE Transactions on Biomedical Engineering, 2011, 2102-2108, vol. 58 No. 7, IEEE Engineering in Medicine and Biology Science, United States.
Leung et al, Automated Sperm Immobilization for Intracytoplasmic Sperm Injection, IEEE Transactions on Biomedical Engineering, 2011, 935-942, vol. 58 No. 4, IEEE Engineering in Medicine and Biology Science, United States.
Liu et al, Automated Microinjection of Recombinant BCL-X into Mouse Zygotes Enhances Embryo Development, Plos One, 2011, e21687, vol. 6 issue 7, Plos, United States.
Serge et al, Dynamic multiple-target tracing to probe spatiotemporal cartography of cell membranes, Nature Methods, 2008, 687-694, vol. 5 No. 8, Nature Publishing Group, New York.
Gold et al, Misconceptions about the causes of cancer, Risk Controversy Series, 2002, 1-141,3, The Fraser Institute, Canada.
Sulston et al, The embryonic cell lineage of the nematode *Caenorhabditis elegans*, Developmental Biology, 1983, 64-119, 100, Academic Press, Inc., United States.
Ganem et al, A mechanism linking extra centrosomes to chromosomal instability, Nature, 2009, 278-282, 460, Macmillan Publishers Ltd., New York.
Shi et al, Chromosome nondisjunction yields tetraploid rather than aneuuploid cells in human cell lines, Nature, 2005, 1038-1042, 437, Macmillan Publishers Ltd., New York.
Steigemann et al, Aurora B-mediated abscission checkpoint protects against tetraploidization, Cell, 2009, 473-484, 136(3), Elsevier, United States.
Uetake et al., Cell cycle progression after cleavage failure: mammalian somatic cells do not possess a "tetraploidy checkpoint," Journal of Cell Biology, 2004, 609-615, vol. 165 No. 5, The Rockefeller University Press, New York.
Sharpless et al, The INK4A/ARF locus and its two gene products, Current Opinion in Genetics and Development, 1999, 22-30, 9, Elsevier Science Ltd., United States.
Lowe et al., Intrinsic Tumour Suppression, Nature, 2004, 307-315, vol. 432, Nature Publishing Group, United States.
Otto, The evolutionary conseuqnces of polyploidy, Cell, 2007, 452-462, 131, Elsevier, United States.
Torres et al, Aneuploidy: cells losing their balance, Genetics, 2008, 737-746, 179, Genetics Society of America, United States.
Weaver et al, The aneuploidy paradox in cell grosth and tumorigenesis, Cancer Cell, 2008, 431-433, 14(6), Elsevier, United States.
Boveri, Zur Frage der Entstehung Maligner Tumoren, 1914, Jena: Verlag Von Gustav Fischer, Germany.
Boveri et al, Concerning the Origin of Malignant Tumours, Journal of Cell Science, 2008, 1-84, vol. 121 supplement 1, The Company of Biologists, United Kingdom.
Gisselsson et al, When the genome plays dice: circumvention of the spindle assembly checkpoint and near-random chromosome segregation in multipolar cancer cell mitoses, Plos One, 2008, e1871, vol. 3 issue 4, Plos, United States.
Holland et al, Boveri revisited: chromosomal instability, aneuploidy and tumorigenesis, Molecular Cell Biology, 2009, 478-487, vol. 10, Macmillan Publishers Ltd., New York.
Vousden et al, p53 in health and disease, Molecular Cell Biology, 2007, 275-283, vol. 8, Macmillan Publishers Ltd., New York.
Junttila et al, p53—a Jack of all trades but master of none, Nature Reviews Cancer, 2009, 821-829, vol. 9, Macmillan Publishers Ltd., New York.
Cicalese et al, The Tumor Suppressor p53 regulates polarity of self-renewing divisions in mammary stem cells, Cell, 2009, 1083-1095, 138, Elsevier, United States.
Livingstone et al. Altered cell cycle arrest and gene amplification potential accompany loss of wild-type p53, Cell, 1992, 923-935, 70, Cell Press, United States.
Fujiwara et al, Cytokinesis failure generating tetraploids promotes tumorigenesis in p53-null cells, Nature, 2005, 1043-1047, 437, Nature Publishing Group, New York.
Cohen et al, Cell proliferation in carcinogenesis, Science, 1990, 1007-1011, vol. 249, American Association for the Advancement of Science, United States.
Brosh et al, When mutants gain new powers: news from the mutant p53 field, Nature Reviews Cancer, 2009, 701-713, vol. 9, Macmillan Publishers Ltd., New York.
Levine et al, The first 30 years of p53: growing ever more complex, Nature Reviews Cancer, 2009, 749-758, vol. 9, Macmillan Publishers Ltd., New York.
Meek, Tumor suppression by p53: a role for the DNA damage response?, Nature Reviews Cancer, 2009, 714-723, vol. 9, Macmillan Publishers Ltd., New York.
Hayflick, Cell biology of aging, The Journal of Investigative Dermatology, 1979, 8-14, vol. 73 No. 1, The Williams and Wilkins Co., United States.
Hayflick, Recent advances in cell biology of aging, Mechanisms of Aging and Development, 1980, 59-79, 14, Elsevier Sequoia S.A., Lausanne, Netherlands.
Wheatley, Aurora-B Phosphorylation in Vitro Identifies a Residue of Survivn That is Essential for its Localization and Binding to Inner Centromere Protein (INCENP) in Vivo, The Journal of Biological Chemistry, 2004, 5655-5660, vol. 279 issue of Feb. 13, The American Society for Biochemistry and Molecular Biology, Inc., United States.
Sheltzer et al, The aneuploidy paradox: costs and benefits of an incorrect karyotype, Trends in Genetics, 2011, 446-453, vol. 27 No. 11, Cell Press, United States.
Bremermann, Reliability of proliferation controls, The Hayflick limit and its breakdown in cancer, Journal of Theoretical Biology, 1982, 641-662, vol. 97 issue 4, Elsevier, United States.

* cited by examiner

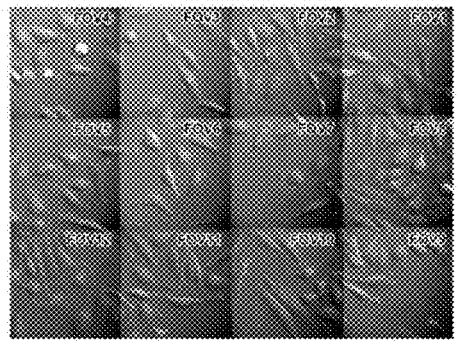
FIG. 3A
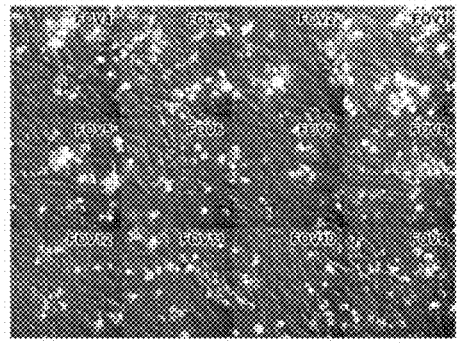
FIG. 3D
FIG. 3B
FIG. 3E
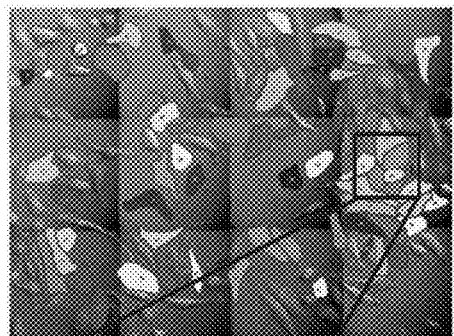
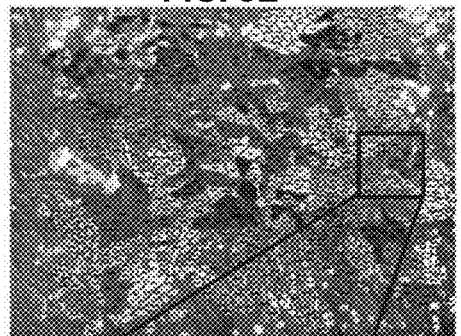
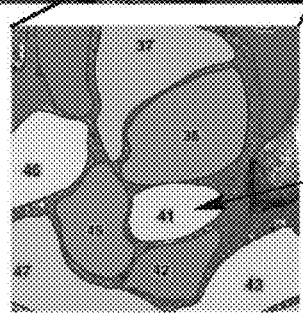
FIG. 3C
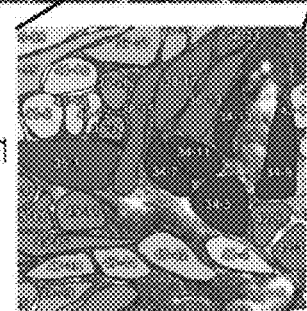
FIG. 3F
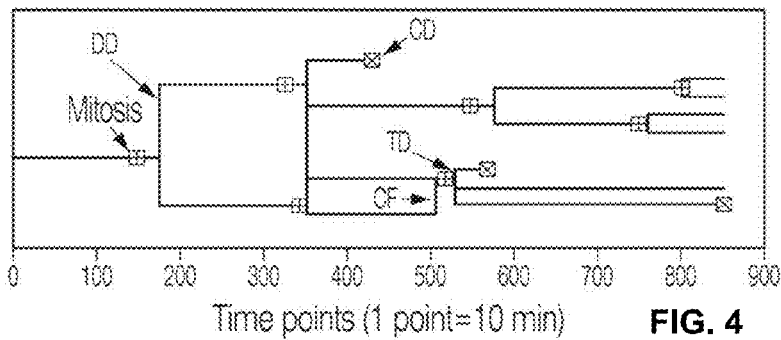
FIG. 4

BIOLOGICAL ASSAYS FOR THE CHARACTERIZATION OF CELLS USING SINGLE-CELL TRACKING AND USES THEREOF

CROSS-REFERENCE TO RELATED APPLICATIONS

This application claims priority under 35 U.S.C. §119(e) of US provisional patent application No. 61/401,121 filed Apr. 30, 2012, the specification of which is hereby incorporated by reference.

FIELD OF THE INVENTION

The invention relates to the field of medicine. More particularly, it relates to biological markers associated with or originated from phenotypical and/or genotypical alteration(s) in a cell and to methods for assessing mammalian cells.

BACKGROUND OF THE INVENTION

The human cancers, which often originate from a single malignantly transformed cell, could be caused by exposure to environmental carcinogens. Since the dose of carcinogens in the environment is substantially low, it is assumed that cellular events leading to transformation cannot readily be detected by currently existing carcinogenicity (in vivo) or genotoxicity (in vitro) tests. Thus, it is still not known well how frequently such transformations are induced by environmental carcinogens. As a compromise, high and lethal doses of test substances have been used in laboratory tests and results obtained with high doses are used to extrapolate the likely effects of lower doses and assess carcinogenic potential. Conceptually, such extrapolation could create complications in the interpretation of results. Firstly, cytotoxicity caused by lethal or high doses could prevent the detection of carcinogenic events, as malignantly transformed cells, which are supposed to be the focus of studies, are also eliminated by cytotoxicity. Secondly, there is no solid evidence that the critical alterations that occur in a small number of cells following exposure to low doses can indeed be extrapolated from responses of cells induced by lethal doses, which could alter the majority of cells. If responses of cells induced by low doses are distinct from that of high doses, extrapolation could lead to inaccurate conclusions. At this moment, there is almost no accurate way to know whether conclusions obtained through extrapolation are correct, as information regarding the responses of cells to low and environmental doses of carcinogens is not available.

One of well-known in vitro tests, the Ames test, which uses histidine deficient salmonella mutants and evaluates genotoxicity by counting the number of revertants produced as a result of gene mutations shows a failure rate of about 55%. Various mammalian cell-based assays, including the sister chromatid exchange test, the mouse lymphoma tk gene mutation assay and the chromosomal aberration test, show good positive rates for known rodent carcinogens (about 70-90%), but also show high positive rates for non-carcinogens (false positive rates; over 70-80%), thereby making the accurate assessment of the carcinogenicity of substances difficult.

In vivo test, i.e. carcinogenicity tests with animals, mainly with rats and mice, also suffers inaccuracy. The life span of rodents is less than 2-3 years. Thus, in order to produce a tumor, which growth in humans often takes over 20 years, within the life time of experimental rodents, high doses or close to lethal doses of substances are often administered despite concerns that such high doses do not represent the situation in humans that are exposed to substantially lower doses of carcinogens. In fact, it has been known that false positive or negative results are likely produced by carcinogenicity tests with experimental animals. Thus, human carcinogens are generally difficult to identify by existing laboratory-based investigations. All of these problems could be related to the lack of information regarding cell responses induced by environmental doses of carcinogens.

There is thus a need for a non-extrapolation method that allows the study of abnormal and rare cellular events induced by environmental doses of carcinogens. Such events could be identified and detected by video recording of live cells (live-cell imaging), tracking of individual cells, creation of cell lineage maps, establishment of cell lineage database and quantitative identification of abnormal and rare cellular events. The majority of currently available live-cell imaging analyses are based on visualization of cells through excitation of fluorophores, e.g. fluorescent proteins (green, red, yellow, etc.), fluorescent dyes, quantum dots, etc. However, excitation of fluorophores is known to be a cause of phototoxicity, hindering the detection of abnormal and rare cellular events.

There is thus a need for a fluorescence-free live-cell imaging technique useful in the determination of quality of mammalian cells and for the study of carcinogenicity of compounds, especially response to low/veritable and environmental doses of carcinogens.

The present invention addresses these needs, as it relates to methods and biomarkers useful in the assessment of compounds, screening of compounds, evaluation and/or control of the quality of cells, etc.

Additional features of the invention will be apparent from review of the disclosure, figures, and description of the invention.

BRIEF SUMMARY OF THE INVENTION

According to a first aspect, the invention is concerned with a method for assessing the condition of a population of cells, comprising:
  culturing a population of mammalian cells;
  tracking individual cells within said population of cells for measuring occurrence of one or more distinctive cellular event(s) in said population of cells and for calculating a frequency of said distinctive cellular event(s); and
  correlating said frequency with condition of the cell population, wherein said frequency is indicative of the presence or absence of phenotypically and genotypically altered cells in said cell population.

The one or more distinctive cellular event may be selected from the group consisting of: dipolar division (DD), tripolar division (TD), quadripolar division (QD), hexapolar division (HD), cell fusion (CF), cell death (CD), incomplete or partial division (IP), cell shape alteration (CSA), nuclear shape alteration (NSA), inner cellular material accumulation (IA), cell enlargement (CE), engulfing (EG), hyper-mobilization (HEM), hypo-mobilization (HPM), prolonged doubling time (PD), and shortened doubling time (SD).

In one embodiment, the culturing step comprises contacting the cells with a candidate carcinogenic compound and the frequency is indicative of carcinogenicity of the candidate carcinogenic compound.

According to a second aspect, the invention is concerned with a method for assessing carcinogenicity of an external event, including but not limited to a candidate compound, comprising:

culturing a population of cells in presence of said external event;

tracking individual cells within said population of cells for detecting in said population occurrence of distinctive cellular event(s) and for calculating a frequency of appearance or not of such distinctive cellular event(s) over a definite period of time; and assessing carcinogenicity of the external event, wherein the calculated frequency is indicative of carcinogenic potential of the external event.

In one embodiment, the step of assessing carcinogenicity comprises comparing the calculated frequency with a control frequency obtained from a population of cells cultured in absence of the external event, including but not limited to a candidate compound. Preferably, the assessing carcinogenicity comprises comparing the calculated frequency of a cell population with a control frequency obtained concurrently from a population of cells cultured in absence of the external event (e.g. candidate compound). Preferably also, the population of cells is cultured in presence of a non-cytotoxic dose or a sub-toxic dose of the external event candidate compound.\

Another related aspect of the invention concerns a method for assessing anti-cancer activity of a potential anti-cancer compound, comprising:

culturing under microscopic observation a population of cells in presence of said candidate anti-cancer compound;

detecting in said population occurrence of distinctive cellular event(s) by tracking individual cells within said population with cell-lineage tracking and imaging device;

calculating a frequency of appearance or not of said event(s) over a certain period of time; and assessing anti-cancer activity of the candidate compound, wherein the calculated frequency is indicative of anti-cancer activity of the candidate compound.

Another related aspect of the invention concerns a method for assessing quality of a population of therapeutic cells, comprising:

obtaining a plurality of cells to be transferred to a patient;

culturing under microscopic observation said plurality of cells;

detecting in said plurality of cells occurrence of distinctive cellular event(s) by tracking individual cells within said population with a cell-lineage tracking and imaging device;

characterizing the cell population as a containing cells of unacceptable quality based on frequency of said distinctive cellular event(s).

This method may further comprise the additional step of eliminating cells of unacceptable quality.

An additional aspect of the invention concerns a method for assessing the condition of a population of cells, comprising:

culturing under microscopic observation a population of mammalian cells;

capturing during said microscopic observation sequential images of said cultured cell population for a sufficient period of time;

indexing a plurality of cells in the captured sequential images for tracking individual cells over a certain period of time;

analyzing the captured sequential images with indexed cells for measuring occurrence of one or more distinctive cellular event(s) in said population of cells and for calculating a frequency of said distinctive cellular event(s); and correlating said frequency with condition of the cell population, wherein said frequency is indicative of the presence or absence of phenotypically and genotypically altered cells in said cell population.

In some embodiments, the cell-lineage tracking and imaging device is a non-fluorescent cell-lineage tracking and imaging device, preferably automated and computer controlled.

Additional aspects, advantages and features of the present invention will become more fully understood from the detailed description given herein and from the accompanying drawings, which are exemplary and should not be interpreted as limiting the scope of the invention.

BRIEF DESCRIPTION OF THE FIGURES

FIG. 2 includes FIG. 2A, 2B, 2C wherein

FIG. 3 includes FIG. 3A, 3B, 3C, 3D, 3E, 3F which are photographs showing a typical panorama view, cell lineage number and cell numbering, in FIG. 3A an example of panorama view (T=1) is shown. In FIG. 3B, each progenitor was numbered. Cells that moved out from FOVs were excluded from numbering. A magnified image of the panorama view (T=1) is shown in FIG. 3C. Cell Lineage 41 is indicated in FIG. 3C. An example of panorama view (T=852) is shown in FIG. 3D. All progeny cells were identified and numbered, in FIG. 3E. In the magnified view shown in FIG. 3F, five surviving progenies of cell lineage 41 (41-4, 41-8, 41-10, 41-12 and 41-14) can be found;

FIG. 4 is a graphical representation of a cell lineage diagram based on data found in FIG. 3, this map corresponds to cell lineage 41 indicated in FIG. 3C. During long-term live cell imaging, progenies entered cell death (CD), dipolar division (DD), tripolar division (TD) and cell fusion (CF);

Figure 8:
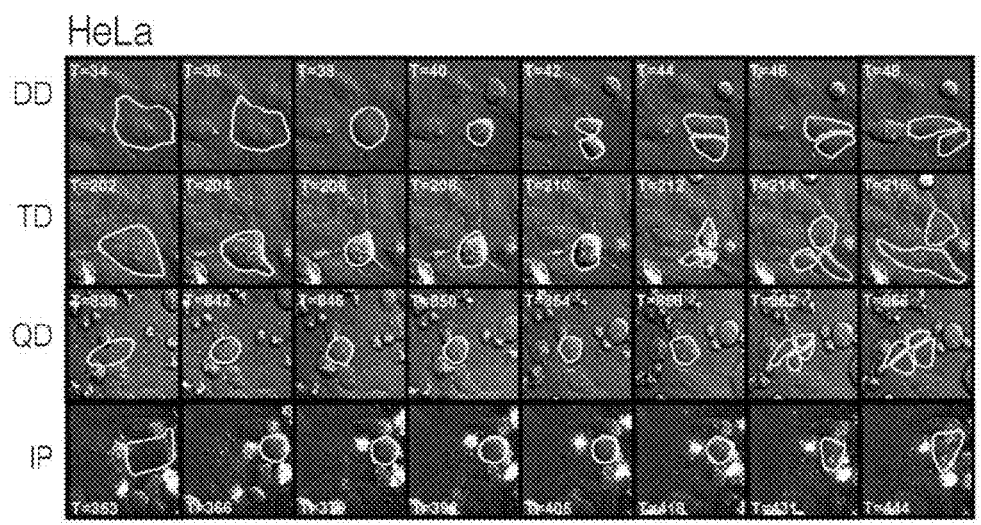
Figure 9:
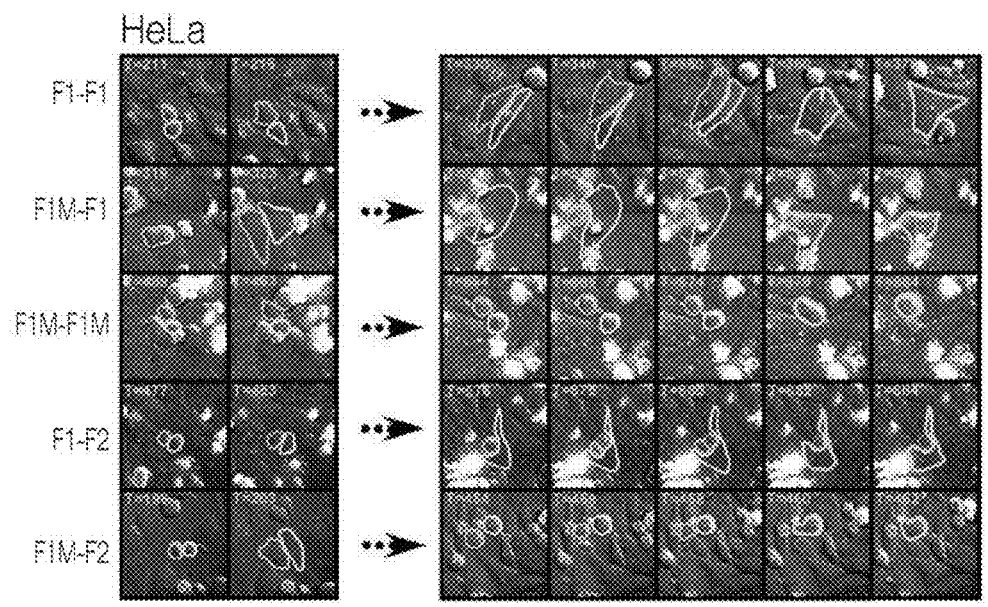
Figure 10:
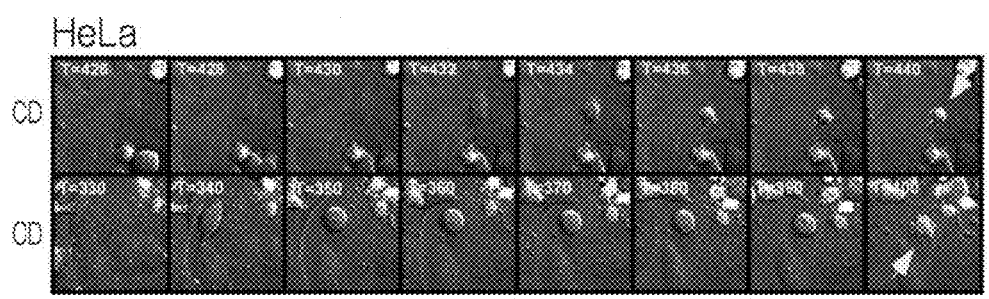

FIG. 8 includes photographs showing the categorization of DD, TD, quadripolar division (QD), incomplete or partial division (IP) for HeLa cells;

FIG. 9 includes photographs showing the categorization of CF, in which HeLa cells in T=1 were defined as F0 and first-level progenies and second-level progenies as F1 and F2, respectively, F1M represents progenies that entered mitosis; and FIG. 10 includes photographs showing the categorization of CD for HeLa cells, including all types of CD regardless of observed patterns, which depend on cell types.

DETAILED DESCRIPTION OF PREFERRED EMBODIMENTS

In the following description of the embodiments, references to the accompanying drawings are by way of illustration of an example by which the invention may be practiced. It will be understood that other embodiments may be made without departing from the scope of the invention.

At this moment, there is almost no accurate way to evaluate the cellular effects and/or response of mammalian cells induced by significantly low and environmental doses of carcinogens. Also, there is almost no non-invasive means for quantitative determination of the quality of cell populations and ensuring that such cell population is free from potentially harmful cells (e.g. cancerous cell).

The present inventors have identified cell biological markers either associated with phenotypical and/or genotypical alteration(s) in a cell. Assessment of those biological markers allows to quantitatively determine the quality of cell populations and finds utility in a variety of methods, including but not limited to, (i) assessing cell condition in general, including cell quality (ii) assessing carcinogenicity of compounds, and (iii) screening for anti-cancer compounds. These markers are distinctive cellular events and they can be detected by a single cell level-based analysis including, but not limited to, long-term live cell tracking with a microscope system.

Distinctive Cellular Events and Cell Condition

As described herein, the inventors have identified distinctive cellular events which frequency in a cell population correlates with the condition of mammalian cells.

Accordingly, a first aspect of the invention concerns a method for assessing the condition of a population of cells, comprising: culturing a population of cells; measuring occurrence of one or more distinctive cellular event(s) in the population of cells and calculating a frequency of said distinctive cellular event(s); and correlating the calculated frequency with condition of the cell population. As used herein, the term "distinctive cellular event", refers to a cellular biological marker which is indicative of the condition of the cells. Examples of distinctive cellular events include, but are not limited to, dipolar division (DD), tripolar division (TD), quadripolar division (QD), hexapolar division (HD), cell fusion (CF), cell death (CD), incomplete or partial division (IP), cell shape alteration (CSA), nuclear shape alteration (NSA), inner cellular material accumulation (IA), cell enlargement (CE), engulfing (EG), hyper-mobilization (HEM), hypo-mobilization (HPM), prolonged doubling time (PD), and shortened doubling time (SD).

The term "distinctive cellular event" also embraces "rare cellular event" i.e. certain distinctive cellular events occurring at such a low frequency that it is not evident in a cell population at a macroscopic level. Particularly, according to particular embodiments the present invention allows observation or detection of rare cellular events that occur once in 16,000 cells during 160 hours observation period, or at a frequency of about 1%-0.1% or less; or at a frequency of about 0.1-0.01% or less; or at a frequency of about 0.01-0.001% or less, where the percentage is Number of rare cellular event/number of Total division×100. In preferred embodiments, the distinctive cellular event occurs at a very low frequency or in a tiny number of cells within vast majority of cells.

"Distinctive cellular events" also include the following: Cell shape alteration is the modification of the overall shape of the cell during observation. Nuclear shape alteration is the modification of the shape of the nucleus of the cell during observation. Inner material accumulation is when a cell contains at least one other cell or engulfs a foreign material such as a microorganism or a particle or forms a structure composed by a protein, a nucleic acid and a lipid. Cell enlargement is when the size of the cell grows during observation without yielding progenies. Hyper-mobilization is when a cell migrates more than the average mobility range for the majority of cells, for example the cell may migrate 200% more than the average mobility rate, Hypo-mobilization is when a cell migrates less than the average mobility rate for the majority of cells, for example the cell may migrate 30% less than the average mobility rate. In another case, a cell could become attached to or could "cuddle" a neighboring cell if its/their mobility rate is low enough. This would also be hypo-mobilization. Prolonged doubling time is when the time between one division and the next division for a particular cell is for example 50% longer than the average time of the majority of cells. Shortened doubling time is when the time between one division and the next division for a particular cell is for example 50% shorter than the average time of the majority of cells.

According to the invention, frequency of the distinctive cellular events in a cell population correlates with the condition of cells. As used herein, the term "condition", when used in association with cell(s) or in association with a population of cells, refers to the general state of the cell, i.e. "normality", quality, integrity, absence of pathogenic alteration of the cell. Normal cellular events include mitosis (M) and dipolar cell division (DD), to the extent that those events occur within an acceptable frequency. According to embodiments of the invention, the condition or general state of cells is assessed by quantitatively detecting one or more distinctive cellular event (s). In a particular embodiment, the term "condition" refers more particularly to presence or absence of an alteration deriving from phenotypical and/or genotypical alteration(s) in a mammalian cell.

In another particular embodiment, the term condition refers more particularly the "therapeutic quality" of a cell, i.e. the cell that can be safely transferred to a mammalian subject with the lowest assessable risk of causing a disease or pathological condition (e.g. tumor, undesirable immune response, infection, etc.). For example, the methods of the invention may find uses to determine that a cell population is acceptable for the future treatment using regenerative medicine, and as such, cell populations contaminated with cancerous cell would generally not be a good quality of cell populations. Cell populations, which have tendency to enter cell death or which show too slow or too fast growth rate also would not be a good cell population. Therefore, in some embodiment the methods of the invention are used for assessing the therapeutic quality of a cell, including but not limited to, ensuring that the cells are not cancerous or infected by a virus (e.g. HIV). Associated embodiments of the invention may provide a means to observe timing of cell infection, timing of uptake of materials by cells or timing of cell-cell (pathogen) contact.

As used herein, the term "frequency", "calculated frequency" or "correlate a frequency" and similar terms, when used in association of the term "distinctive cellular event(s)", refers to a quantitative assessment of occurrence of such events (i.e. number of occurrence over a certain period of time and Cell Quality Index (CQI) value determined based on the number of occurrence). As used herein, the term "measuring occurrence", "detecting occurrence" or "assessing occurrence" when used in association of the term "distinctive cellular event(s)" refers to detecting and/or quantifying presence and/or absence of such events. According to embodiments of the inventions, measuring occurrence typically comprises calculating a frequency of appearance (or absence thereof) of such events over a definite or limited period of time or determining value of CQI. As indicated hereinafter, the frequency of appearance of distinctive cellular event(s) can be correlated with cell condition and in particular embodiments the calculated frequency is indicative of the presence or absence of an alterations associated with phenotypically and genotypically altered cells in the cell population. For instance, in a particular embodiment, occurrence of tripolar division (TD) (i.e. a higher frequency or higher CQI value) represent the risk of the presence (or increased number) of cells, which have an abnormal characteristic.

Those skilled in the art will appreciate that the selection of the distinctive cellular event(s) to be detected will vary according to the cell population (e.g. skin cells, brain cells, liver cells, etc.), or the desired test or targeted analysis (e.g. viability, carcinogenic potential, or cytotoxic potential etc.). For instance, in one particular embodiment, tripolar division (TD), quadripolar division (QD), hexapolar division (HD), cell fusion (CF) are used to determine cell quality.

In preferred embodiments the cells are observed for a certain period of time for measuring occurrence or frequency of the distinctive cellular event(s). Typically, the cells should be under observation for a sufficient period of time, for instance a period of time long enough for at least one progenitor to divide into progenies. For example, the period of time could be 7 minutes, 100 minutes, 160 hours, 330 hours, one month, etc.

Various methods, techniques and calculations can be used for assessing the condition of a population of cells, and more particularly for quantitatively assessing occurrence or frequency of the distinctive cellular event(s) according to the invention. As described herein after, in preferred embodiments, quantitative assessment of occurrence or frequency of the distinctive cellular event(s) comprises non-fluorescent microscopic observation, tracking and imaging of a plurality of cells. More preferably, a computer-implemented method and system is used.

In preferred embodiments, the one or more distinctive cellular event(s) are assessed within normal events and/or by using normal cells as reference or control. For instance, a "normal" frequency of distinctive events can be obtained by determining the frequency of distinctive events that occur in reference or control cells.

Assessment of occurrence and/or frequency of distinctive cellular events may comprise obtaining a "cell quality index" (CQI). The term cell quality index or CQI can be defined as an index determined by taking into account the number of distinctive cellular events and normal events occurring during the monitoring of cells. By employing particular constants, CQI reflects the overall growing ability of cells and is indicative of the tendency to have certain abnormality of a cell lineage. CQI can be determined for cells composing an entire cell lineage, or part of cells composing the lineage. In addition, by determining average CQI, overall characteristics of cells population can be determined.

In a preferred embodiment, the CQI takes into account the on-going frequency of distinctive cellular events of each cell lineage and it can be calculated using the two formulas:

$$CQI = [A \times \text{number of dipolar cell division (DD)}] + [B \times \text{number of tripolar cell division (TD)}] + [C \times \text{number of quadpolar cell division (QD)}] + [D \times \text{number of hexapolar cell division (HD)}] + [E \times \text{number of fusion (CF)}] + [F \times \text{number of cell death (CD)}] + [G \times \text{number of incomplete and number of partial cell division (IP)}] + [H \times \text{number of cells showing cell shape alteration (CSA)}] + [I \times \text{number of cells showing nuclear shape alteration (NSA)}] + [J \times \text{number of cells showing inner cellular material accumulation (IA)}], + [K \times \text{number of cells showing cell enlargement (CE)}] + [L \times \text{number of cells showing engulfing (EG)}] + [M \times \text{number of cells showing hyper-mobilization (HEM)}] + [N \times \text{number of cells showing hypo-mobilization (HPM)}] + [O \times \text{number of cells showing prolonged doubling time (PD)}] + [P \times \text{number of cells showing shortened doubling time (SD)}] \quad \text{(Formula 1)}$$

wherein B, C, D, E, F, G, H, I, J, K, L, M, N, O and P are real numbers between −1.000 and +1.000; and $$CQI = ([B \times \text{number of tripolar cell division (TD)}] + [C \times \text{number of quadpolar cell division (QD)}] + [D \times \text{number of hexapolar cell division (HD)}] + [E \times \text{number of fusion (CF)}] + [F \times \text{number of cell death (CD)}] + [G \times \text{number of incomplete and number of partial cell division (IP)}] + [H \times \text{number of cells showing cell shape alteration (CSA)}] + [I \times \text{number of cells showing nuclear shape alteration (NSA)}] + [J \times \text{number of cells showing inner cellular material accumulation (IA)}], + [K \times \text{number of cells showing cell enlargement (CE)}] + [L \times \text{number of cells showing engulfing (EG)}] + [M \times \text{number of cells showing hyper-mobilization (HEM)}] + [N \times \text{number of cells showing hypo-mobilization (HPM)}] + [O \times \text{number of cells showing prolonged doubling time (PD)}] + [P \times \text{number of cells showing shortened doubling time (SD)}]) / ([A \times \text{number of dipolar cell division (DD)}] + [B \times \text{number of tripolar cell division (TD)}] + [C \times \text{number of quadpolar cell division (QD)}] + [D \times \text{number of hexapolar cell division (HD)}]) \quad \text{(Formula 2)}$$

wherein A, B, C, D, E, F, G, H, I, J, K, L, M, N, O and P are real numbers between −1.000 and +1.000.

In the formulas above, A, B, C, D, E, F, G, H, I, J, K, L, M, N, O and P are constants which value is set to develop a formula and obtain a CQI which can represent particular characteristics of a given type of cell population (e.g. skin cells, brain cells, established cultured cell lines such as HeLa cells etc.) or a particular test or targeted analysis (e.g. viability, carcinogenic potential, or cytotoxic potential etc.). These constants may be identified or calculated by taking into account the frequency of distinctive events. Those skilled in the art can set these constant according to a desired use or results and develop new CQI formula as needed. For instance, in Formula 1 the DD value is such that the CQI provides a general cell condition, whereas in Formula 2, DD is used as a reference to make emphasis on a particular event, other than DD.

Therefore, the "frequency" can be determined by focusing on particular distinctive events. For instance: "frequency= (TD+QD+HD)/(DD+TD+QD+HD)" can be used to determine the carcinogenic potential of compounds. This calculated frequency can be considered as a simplified version of CQI (Formula 2), where A=1, B=1, C=1, D=1 and others constants are 0. In one embodiment, average CQI calculated with constants, A=1, B=1, C=1, D=1 and others are 0, is used to determine carcinogenic potential of cells populations. In another embodiment, the constants associated with TD, HD, QD, CF are not zero since TD, HD, QD, CF are used to determine cell quality.

Table A provides some examples of the distinctive cellular events which can be detected (for calculating a frequency thereof according to the methods of the invention) and used, as necessary, for obtaining a CQI:

TABLE A

| Desired test or targeted analysis | Distinctive cellular events |
|---|---|
| Viability | DD, TD, QD, HD, CF, CD, IP, CSA, NSA, IA, CE, EG, HEM, HPM, PD, SD |
| Carcinogenic potential | TD, QD, HD, CF, IP, CSA, NSA, CE, SD |
| Cytotoxic potential | CD, CE, PD |
| Anti-cancer | TD, QD, HD, CF, CD, IP, SD |
| Cell quality | TD, QD, HD, CF, CD, IP, CSA, NSA, IA, CE, EG, HEM, HPM, PD, SD |

Assessment of occurrence and/or frequency of a distinctive cellular event(s) may comprise comparing the calculated frequency with a "control" frequency or the calculated CQI value with a "control" CQI obtained from a control population of cells.

Various types of cells can be used according to the invention, such as eukaryotic cells in generals. Preferably, the cells are mammalian cells. As used herein, the "mammal" or "mammalian" includes animals (e.g. cats, dogs, horses, pigs, cows, goats, sheep, rodents, e.g., mice or rats, rabbits, squirrels, bears, primates (e.g., chimpanzees, monkeys, gorillas, and humans)), and transgenic species thereof. More preferably, the cells are human cells. Suitable cells also include primary cultured mammalian cells, established mammalian cells, adherent cells, cells from immortalized cells lines, differentiated cells derived from stem cells, stem cells or freshly isolated cells from tissue.

According to some aspects, the invention concerns methods for assessing cell quality. In particular embodiments, the invention embraces methods and non-invasive means to quantitatively determine the quality of cell populations and/or to ensure that a given population of cells is free from potentially harmful cells (e.g. cancerous cell). For instance, according to the invention, the population of cells may be therapeutic mammalian cells (e.g. neurons, retina, skin, etc.) to be transferred to a mammalian subject (e.g. differentiated cells derived from embryonic stem cells and induced pluripotent stem cells (iPS cells)).

According a particular embodiment, the method for assessing quality of a population of therapeutic cells, comprises: obtaining a plurality of cells to be transferred to a patient; culturing under microscopic observation the plurality of cells; detecting in the plurality of cells occurrence of distinctive cellular event(s) by tracking individual cells within said population with a cell-lineage tracking and imaging device; characterizing the cell population as a containing cells of unacceptable quality based on presence and/or frequency of the distinctive cellular event(s).

The method may further comprises the step of eliminating undesirable cells and/or cells of unacceptable quality, for instance by discarding the whole lot of cells or by eliminating individual cells by suitable methods and devices such as laser, microwave or by microcapillary system. In some embodiments, the cell-lineage tracking and imaging device is a non-fluorescent cell-lineage tracking and imaging device, preferably automated and computer controlled.

Comparative studies can also be carried out to test the effect of an external event or compound on the occurrence and/or frequency of a distinctive cellular event. For instance, the occurrence and/or frequency may be calculated for cells treated or not with the following: inorganic substances, biological materials, proteins/enzymes, factors, nucleic acids, glycans, virus, bacteria, parasites, metals ions and/or particles, ionizing radiations, lights, magnetic fields, to name a few. The cells can also be pre-exposed to reagents or factors prior the treatment or co-exposed to reagents, factors or fraction containing drug metabolizing enzymes. In some cases, different types of cells can be used.

Assessment of occurrence and/or frequency of a distinctive cellular event according to the invention may also be combined with additional screening techniques or biological markers. For instance, cells may further be tested for the presence and/or expression level of other cell markers or genes which are typically absent from normal cells, including but not limited to, oncogenes, tumor suppressors, repair enzymes and factors, DNA replication regulator, cell cycle regulator, transcription regulators, proteins involved in cytokinesis, structural components of cells, and the like.

Methods for Assessing Carcinogenicity

According to another aspect, the invention concerns a method for assessing carcinogenicity of an external event, including but not limited to a candidate compound. As used herein, the term "external event" refers to any kind of event, which can alter a cell. According to the invention, external events include, but are not limited to, a candidate compound, microorganisms such as virus, bacteria, parasites, ionizing radiations, lights, magnetic fields, to name a few. In preferred embodiments, the external event is a candidate compound. As used herein, the term "candidate compound" refers to any kind of compound to be tested according to any of the methods of the invention. Examples of candidate compounds include, but are not limited to, potential carcinogenic agent, peptide, pharmaceuticals (isolated molecules or chemically synthesized), natural products, chemically synthesized compounds, metals ions, particles, etc.

According to one embodiment, the method for assessing carcinogenicity comprises: culturing a population of cells in presence of a candidate compound; detecting in the cell population occurrence of distinctive cellular event(s) and calculating a frequency of appearance or not of such event(s) over a definite period of time; and assessing carcinogenicity of the candidate compound.

According to this particular aspect of the invention, the calculated frequency is indicative of carcinogenic potentials of the candidate compound. Indeed, for some distinctive cellular events, an increased frequency reflects a higher carcinogenic potential and a lower frequency reflects a lower (or absence) of carcinogenic potential. For some distinctive cellular events, it is the opposite.

Table B provides some examples of the distinctive cellular events, of which calculated frequency is not changed (+/−), increased (+) and reduced (−) by exposure of cells to possible carcinogenic substances:

TABLE B

| Distinctive cellular events | Calculated frequency |
|---|---|
| DD | +/− or + |
| TD | + |
| QD | + |
| HD | + |

TABLE B-continued

| Distinctive cellular events | Calculated frequency |
|---|---|
| CF | + |
| CD | − or +/− |
| IP | +/− or + |
| CSA | +/− |
| NSA | +/− |
| IA | +/− |
| CE | +/− |
| EG | − or +/− |
| HEM | +/− |
| HPM | +/− |
| PD | +/− |
| SD | + |

In particular embodiments, the candidate compound is tested for assessing any existing or suspected carcinogenic potential and/or cytotoxicity. In other particular embodiments, the candidate compound is or could be a carcinogenic agent and it is tested for assessing and/or quantifying potential of known carcinogenic activity.

Various methods, techniques and calculations can be used for assessing the carcinogenicity of the candidate compound, and more particularly for quantitatively assessing occurrence or frequency of the distinctive cellular event(s) in response to a candidate compound. As described hereinafter, in preferred embodiments, such a quantitative assessment comprises non-fluorescent microscopic observation, imaging and tracking of a plurality of cells. More preferably, a computer-implemented method and system is used.

In preferred embodiments, assessing the carcinogenicity comprises comparing the frequency calculated in presence of the candidate compound with a control frequency obtained from a control population of cells, i.e. cells cultured in absence of the candidate compound. In some embodiments, the control frequency is an average value obtained from untreated and/or control cells.

In related aspects, the invention relates to methods and means to establish a minimal carcinogenic dose of a compound. For instance, in accordance with certain embodiments, the invention may help identify which compound acts as potential carcinogens under chronic or long exposure conditions (i.e. long incubation period) (i) at a sub-toxic dose (i.e. a low dose or even very low dose) and/or (ii) at a non-toxic dose. Therefore, it is possible to establish a minimal dose at which a particular distinctive cellular event may occur and/or what the minimal carcinogenic dose for a given compound is. For instance, the minimal dose may be calculated by carrying out dose-response experiments. Accordingly, some aspects of the invention relate to a method for identifying a sub-toxic dose and/or a non-toxic dose of a candidate compound.

As used herein the term "sub-toxic dose" means a dose, which induces cell death and/or inhibits growth in some cells while allowing cell division in at least a portion of the cell population. Therefore, despite the fact that some cell death and/or cell growth inhibition occur, it is generally not observable macroscopically such that cell population maintenance or growth is observed at the macroscopic level (i.e. 100% or more of original cell number is achieved). In various embodiments, a compound is at its sub-toxic dose when it is present at a dose that causes reduction of cell viability determined by CQI compared to that of non-exposed cells, e.g. the reduction is between about 0% —about 50%, or about 10%-40%.

As used herein the terms "non cytotoxic dose" mean a dose that does not reduce cell viability determined by CQI compared to that of non-exposed cells. Therefore, in particular embodiments, a compound is at its non-toxic dose when viability determined by CQI is within the range, which does not show any statistically significant difference with CQI, which is determined with non-treated cells.

In a particular embodiment, the sub-toxic dose and/or a non-toxic dose of the candidate compound (e.g. a compound causing distinctive cellular events) is determined by testing the compound at different doses (e.g. dose-response experiments). Knowing the sub-toxic dose and/or a non-toxic dose of a candidate compound may find various useful applications. For instance, it may allow distinguishing between non-carcinogenic compounds and carcinogenic compounds and increasing accuracy in evaluation of carcinogenic potential of a tested substance. Further, it also may allow distinguishing between anti-cancer drugs that are mutagenic or that may be cytotoxic or inducing secondary cancers from anti-cancer drugs that are safer for administration in human patients.

The methods for assessing the carcinogenicity according the invention may also be combined with existing methods such as the Ames test, in vivo toxicology studies, the sister chromatid exchange test, the mouse lymphoma tk gene mutation assay, and other suitable test known in the art.

Methods for Screening Anti-Cancer Compounds

According to another aspect, of the invention concerns a method for assessing anti-cancer activity of a potential anti-cancer compound. As used herein, the term "potential anti-cancer compound" refers to any kind of molecule suspected to possess beneficial anti-cancer activity. Examples of potential anti-cancer compounds include, but are not limited to, natural and synthetic molecules, peptides, pharmaceuticals, natural products and extracts, etc. In particular embodiments, the potential anti-cancer compound is a potential anti-cancer drug and it is tested for assessing its therapeutic activity.

According to one embodiment, the method for assessing anti-cancer activity comprises: culturing under microscopic observation a population of cells in presence of a candidate anti-cancer compound; detecting in the cell population occurrence of distinctive cellular event(s) with a non-fluorescent cell-lineage tracking and imaging device; calculating a frequency of appearance or not of said event(s) over a certain period of time; and assessing anti-cancer activity of the candidate compound.

According to this particular aspect of the invention, the calculated frequency is indicative of the anti-cancer activity of the potential anti-cancer compound. Indeed, for some distinctive cellular events (e.g. cell division), a lower frequency reflects a greater anti-cancer activity. For some distinctive cellular events, it is the opposite.

Table C provides some examples of the distinctive cellular events, of which calculated frequency are not changed (+/−), increased (+) and reduced (−) by exposure of cells to substances having anti-cancer potential:

TABLE C

| Distinctive cellular event | Calculated frequency |
|---|---|
| DD | +/− |
| TD | − |
| QD | − |
| HD | − |
| CF | − |
| CD | + |
| IP | − or +/− |
| CSA | +/− |
| NSA | +/− |
| IA | +/− |
| CE | +/− |
| EG | +/− |

TABLE C-continued

| Distinctive cellular event | Calculated frequency |
|---|---|
| HEM | +/− |
| HPM | +/− |
| PD | + |
| SD | − or +/− |

Various methods, techniques and calculations can be used for assessing the anti-cancer activity of the potential anti-cancer compound, and more particularly for quantitatively assessing occurrence or frequency of the distinctive cellular events. As described hereinafter, in preferred embodiments, such a quantitative assessment comprises non-fluorescent microscopic observation, tracking and imaging of a plurality of cells. More preferably, a computer-implemented method and system is used.

In preferred embodiments, assessing the anti-cancer activity comprises comparing the frequency calculated in presence of the potential anti-cancer compound with a control frequency obtained from a control population of cells, i.e. cells cultured in absence of the potential anti-cancer compound.

In related aspects, the invention relates to methods and means to establish a minimal threshold of anti-cancer activity. For instance, in accordance with certain embodiments, the invention may help identify which compound acts as anti-cancer drug under chronic or long exposure conditions (i.e. long incubation period) at different doses. Therefore, it is possible to establish a minimal dose at which a particular distinctive cellular event related to cancer depletion may occur and/or what is the lowest dose of an anti-cancer drug that can be used, while maintaining therapeutic activity. In some embodiment, establishing the minimal dose comprises carrying out dose-response experiments.

Knowing the lowest active dose of an anti-cancer drug, while maintaining therapeutic activity, may find various useful applications. For instance, it may allow ensuring valuable therapeutic efficacy in patients, while minimizing undesirable side effects (e.g. toxicity, nausea, immune response, etc.). It may also be useful for assessing a possible risk of recurrent tumor formation.

The methods for assessing the anti-cancer activity according the invention may also be combined with existing methods such as the Ames test, in vivo toxicology studies, the sister chromatid exchange test, the mouse lymphoma tk gene mutation assay, and other suitable test known in the art.

Systematic Observation and Tracking of Single Cells

In preferred embodiments, quantitative assessment of occurrence or frequency of the distinctive cellular event(s) according to the various methods described herein comprises non-fluorescent microscopic observation, imaging and tracking of a plurality of cells.

The present invention is not limited to a particular system. Different manual, semi-automatic or automatic apparatus, microscope, software, image analyzer, etc. may be used. Suitable techniques and apparatus are described in International patent application No. PCT/IB2011/054436 filed on Oct. 7, 2011 entitled "Apparatus for systematic single cell tracking of distinctive cellular events", which is incorporated herein by reference in its entirety.

Figure 1:
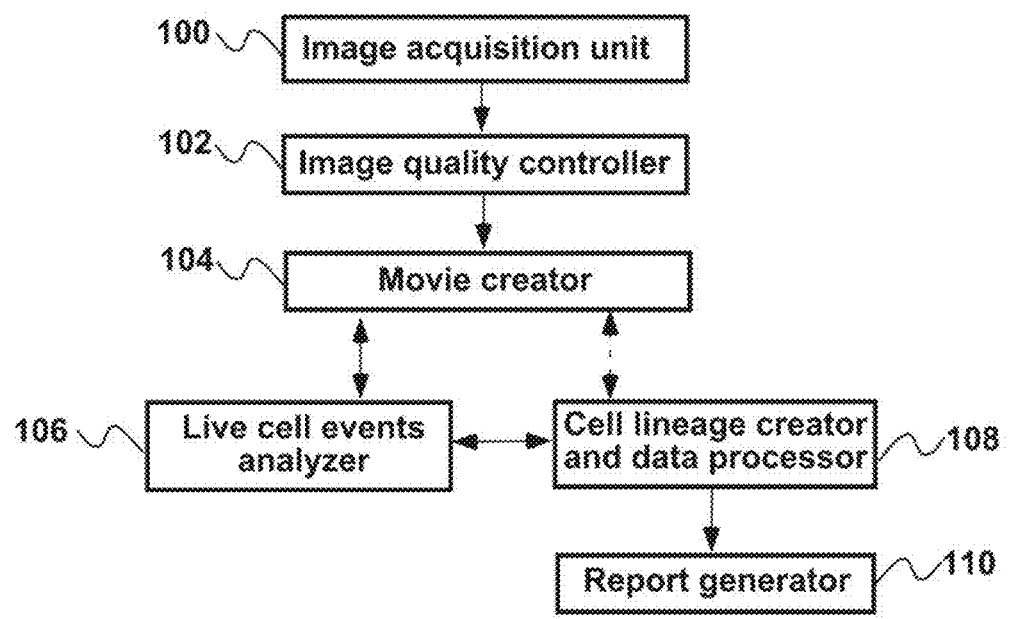
FIG. 1 is a block diagram showing an example of an apparatus for analysis of distinctive cellular events according to an embodiment of the invention.
Figure 2A:
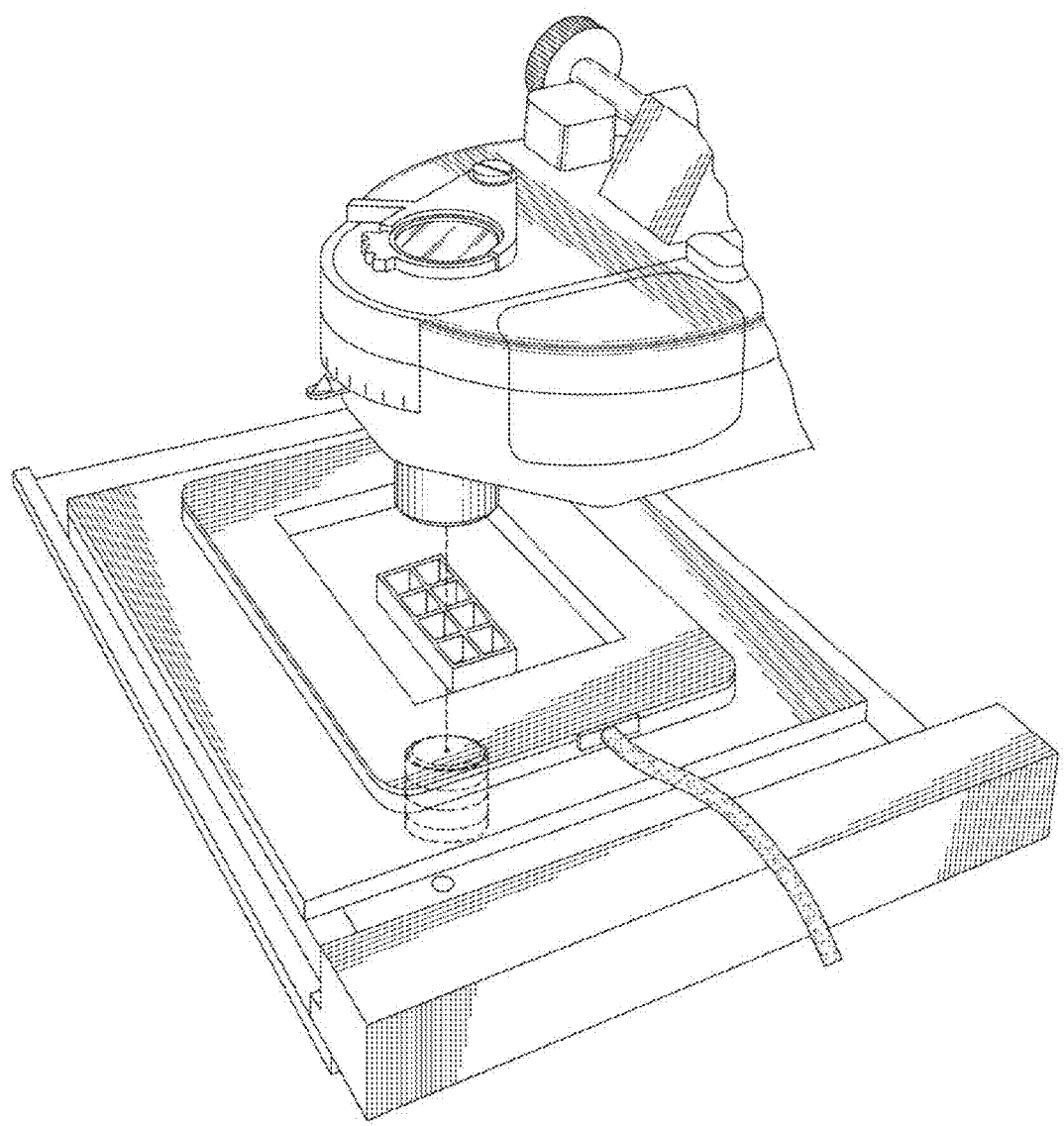
FIG. 2A is a graphical representation of the apparatus of FIG. 1.

Nevertheless, the subject matter described in that PCT is preferred according to the present invention. Briefly, FIG. 1 is a block diagram illustrating an apparatus for analysis of distinctive cellular events. Because such events can occur any moment during cell culture, this apparatus creates a cell imaging movie of treated and non-treated cells, and analyzes recorded cells individually. The Image acquisition unit (100) is composed of a microscope, a CCD camera, a light source, optical filters and elements, a coupler for enlargement of images, an environmental chamber, an adaptor to hold multiwell culture chamber, a X-Y stage and a Z-drive. The light source can be halogen light or LEDs, which create white light or emit some range of visual wavelength such as near infrared. The environmental chamber allows carrying out cell culture on microscope stage for a prolonged period of time, for example for at least 160 hrs at the desired temperature, concentrations of oxygen, carbon dioxide, and nitrogen gas and humidity. The cells are illuminated by a method, which allows visualizing cell structures. The illumination method can be Differential interference contrast (DIC). DIC microscopy, also known as Nomarski Interference Contrast (NIC) or Nomarski microscopy, is an optical microscopy illumination technique used to enhance the contrast in unstained, transparent samples. DIC works on the principle of interferometry to gain information about the optical path length of the sample, to see otherwise invisible features. A relatively complex lighting scheme produces an image with the object appearing black to white on a grey background. FIG. 2A is a graphical representation of the DIC microscope.

The image acquisition unit (100) is controlled by software, which contains drivers for light source, shutters, filters, CCD camera, the X-Y stage and the Z-drives or others, which are necessary to obtain images of cells. The software also has ability to generate raw image data files from at least 100 of multiple fields of views every 10 min or less with multiple z-stacks, for example 20 z-stacks. Any types of software, such as, for example, Metamorph™ or Volocity™, which can drive the microscope system can be used.

Figure 2B:
FIG. 2B is a graphical representation of the wells of the chambered coverglass.
Figure 2C:
FIG. 2C is a graphical representation of the field-of-views of the wells of the chambered coverglass.

The Image acquisition step (100) is carried out by performing a series of consecutive sub-steps: Cell plating (200), Setting of imaging area (202), Setting of image acquisition frequency (204), Cell treatment (206), Illumination of cells (208), Acquisition of cell image (210) and Generation of imaging data (212). The order of steps 202, 204 and 206 can be changed. This process starts by the cell plating (200). A certain number of cells, e.g. 5000 cells per one well of 8-well chamber, is plated into each well of multi-well chamber. The selection of imaging area (202) is carried out in order to find an area, which contains desired number of cells in a certain square micron meters. The number of cells can be any number of cells that fit to a well (e.g. 100 cells or more; 1000 cells or more; 10 000 cells or more). If the image of the square micron meter cannot be obtained by one image acquisition, multiple field of views are arranged to cover the area. FIG. 2B is a graphical representation of the wells of the chambered coverglass. FIG. 2C is a graphical representation of the field-of-views of the wells of the chambered coverglass. The image acquisition can be controlled to acquire images of each field-of-view in each well at a predetermined frequency. In the example embodiment of FIG. 2, there are 15 field of views per well and 8 wells in the chambered coverglass, for a total of 120 field of views. Therefore, the stage could be moved to allow acquisition of the image of the first field of view (FOV1) of the first well (W1), to the last field of view (FOV15) of W1 and on to FOV1 of the second well (W2), all the way to FOV15 of the last well (W8) and then back to FOV1 of W1. The image capture can be at a rate of every 10 minutes for each field of view.

The setting of the image acquisition frequency (204) is determined based on the mobility of cells. At the frequency for the image acquisition, a position of majority of cells in one image overlaps with the same cells in the next image. Because the mobility of each cell can be changed time to time and from cell to cell, the required % of overlap can be varied. In the Cell treatment (206), cells in each wells are either treated or not treated. One well can serve as a control. In the Illumination of cells (208), cells are illuminated by light with wavelengths, which are non- or less toxic for cells in order to minimize light-derived phototoxicity caused by ultra violet light or emission light from a fluorophores exited by their appropriate wavelength of light. Visible wavelength or near infrared are used for instance.

The Acquisition of cell image (210) is carried out by a way, which allows visualizing cellular structures, including nucleolus, nucleoli, mitochondria, cell granules, cell peripheries, outline of cells, shadow created by cells and/or light-reflecting parts of cells. At each field of view, images of planes at various depths within the sample (referred as to z-stacks) are taken to capture from the top to the bottom part of cells. The number of z-stacks is depending on the height of cells and the extent of focal plane drift, which often occurs during the long-term imaging of cells. Thus, minimal number of z-stacks is 1 and the 21 z-stacks are taken for HeLa cells for instance. The Generation of imaging data (212) creates gray scale images, which have graphic format of e.g. TIFF, JPEG, EPS, PICT, or BMP.

The Image quality controller (102) receives image files from the Image acquisition unit (100). After adjustment of contrast, selection of focused images, if multiple images acquired from each field of view are needed to be combined into one image file, these images are stitched. Resulting image files are transferred to the Movie creator (104).

The Image quality controller (102) related step is carried out by performing a series of consecutive sub-steps: Image background correction (300), Focused image identification (302), Image file arrangement (304), Multiple image position adjustment (306) and multiple file image stitching (308). The order of steps 300, 302 and 304 can be changed. Steps 300, 306, and 308 can be skipped if these steps are not required. Briefly, the Image background correction (300) carries out by subtraction of background images from images created by the Image acquisition unit (100). The background images can be ones prepared by image acquisition of corresponding multi-well chamber, which does not contain cells. Then, image contrast is adjusted by setting appropriate mean value and lower and higher threshold value of gray scale images. The Focused image identification (302) selects the best-focused or the images closed to the best-focused ones among multiple z-stacks, which cover top-to-bottom part of cells. If multiple fields of views are set by the Selection of imaging area (202), the Image position adjustment (306) positions the images, which correspond to all fields of views, based on the X-Y position data recorded by image acquisition software. Then, positions of the image are adjusted. If X-Y position data is not available, image position adjustment can be carried out manually. The Multiple image stitching (308) receives adjusted X-Y position data from the Image position adjustment (306) and merges individual images into one image file.

The Movie creator (104) receives imaging files from the Image quality controller (102) and arranges files into an image sequence for movie. Movie creator (104) related step is carried out by performing a series of two consecutive sub-steps: stitched image file arrangement (400) and image sequence creation (402). Briefly, the Stitched image file arrangement (400) organizes image files based on the well numbers of the multiwell chamber. The Image sequence creation (402) orders the stitched image files following the order of image acquisition to create an image sequence. Image sequence file number, which starts from 1, is assigned to each image file.

The Live cell events analyzer (106) receives image sequence files from the Movie creator (104). Among sequenced image files created by the Image sequence creation (402), an image file, which is designated as the Time point 1, is selected. The Time point 1 can be the image, which is acquired immediately after the Cell treatment (206). Thus, the Time point 1 can be the Image sequence file 10 for instance. Following Image sequence files can be Time point 2, Time point 3 etc. Then, cell lineage numbers are assigned to cells in the image of the Time point 1. Cells in the Time point 1 are designated as Progenitors. Each Progenitor and its progenies are tracked. Cellular structures, which are recorded by the Acquisition of cell image (210), are used as markers to track cells. The tracking can continue until to the Time point End, which is the last image files used for cell tracking During the tracking, if normal and distinctive cellular events occur, these events are indexed. Then the Live cell events analyzer (106) creates a database, which contains information of cells, e.g. the indexed data and Time point number and X-Y position of cells.

The Live cell events analyzer (106) related step is carried out by performing a series of consecutive sub-steps: Progenitor position finding (500), Tracking of progenitor (502), Identification of normal events of progenitor (504), Identification of distinctive events of progenitor (506), Progeny identification (508), Tracking of progeny (510), Identification of normal events of progeny (512), Identification of distinctive events of progeny (514), Data verification (516) and Database entry (518). Order of Steps 502, 504 and 506, and Steps of 508, 510 and 512 can be changed. Steps 502, 504 and 506 apply to all Progenitors. Steps 508, 510 and 512 apply to all progenies. The Progenitor position finding (500) assign cell lineage numbers to all or part of cells found in the Time point 1. The cell lineage number associates with X-Y position of cells in the image. In addition to cell lineage number, a cell number is assigned and the number of Progenitor is "0". During the process of the Tracking of progenitor (502), X-Y positions of each cell in the following Time point are determined. If cells move out of the image, the cells are marked with "out of frame" or OF. If there are cells, which move into an image, these cells can remain untracked or can alternatively be tracked. The Identification of normal events of progenitor (504) indexes normal cellular events as defined herein. Indexed data associates with the Time point number and X-Y position of cells. The Identification of distinctive cellular events of progenitor (506) indexes distinctive cellular events as defined herein. Each distinctive cellular event can be subdivided if more precise information is required. For example, cell death can be sub-indexed by mitotic catastrophe and cell death occurred during G1 phase. Indexed data associates with the Time point number and X-Y position of cells. If the events lead to the cell division, created progenies are identified by Progeny identification (508). The cells numbers are assigned to these progenies. The events, which can lead to the formation of progenies, are DD, TD, QD and HD. Tracking of progeny (510), Identification of normal events of progeny (512) and Identification of distinctive cellular events of progeny (514) are equivalent to the Steps 502, 504 and 506 of Progenitors. If the progenies produced their own progenies, Steps 508, 510, 512 and 514 are carried out for the progenies. These steps can be repeated until image reached to the Time point End. After tracking of a progenitor and all of its progenies, X-Y position, indexed data and information for the linking of the Progenitor to all of its progenies are verified by the Data verification (516). If errors are identified, relevant Steps, e.g. Steps 502, 504 and 506 and/or Steps 508, 510, 512 and 514, are repeated. Such errors can be loss of cell tracking and mixing up one cell to another. Resulting data is entered into a database by the Database entry (518). The database contains cell lineage number, cell number, X-Y position, Time point number, indexed event and information, which determine the relationship of each cell.

The Cell lineage creator and data processor (108) receives data, which are entered into database by the Live cell events analyzer (106). Time point number, indexed events and data indicating relationships of one cell to other cells are used to create cell lineage maps. Various parameters, for example, cell growth rate, doubling time and frequency of cell death, cell fusion and abnormal cell division are determined. By mathematical and statistical calculation by applying certain biases to particular indexed events or doubling time, characteristics of distinctive and/or normal events of cell population are also determined. Analyzed data are entered into master database and data, which are already entered into the database, are used to evaluate the effect of treatment on cells.

The Cell lineage creator and data processor (108) related step is carried out by performing a series of consecutive sub-steps: cell lineage map creation (600), Basal data analysis (602), Optional data analysis (604) and Master database search (606). Briefly, the Cell lineage map creation (600) collects the cell lineage numbers, cell numbers, Time point numbers and indexed event data of Progenitors and their progenies from the database generated by the Live cell events analyzer (106). Cell numbers are used to determine the drawing order of each cell. The Basic data analysis (602) analyze cell growth rate, doubling time and the frequency of cell death, cell fusion, normal cell division and abnormal cell division. Other event types can also be included into this basic data analysis. The Optional data analysis (604) performs mathematical calculation by applying certain biases to particular events and/or statistical analysis.

A CQI can be calculated by the Formula 1 or Formula 2 as described previously. The resulting CQI can be used to evaluate viability or individuality of cells derived from a progenitor. Different formula and constants can be used for the calculation. Resulting analyzed data are entered into the master database. Data in the database can be organized by cell type, treatment and/or dose. The master database search (606) collects relevant data from the master database in order to evaluate the effect of treatment on cells.

The Reports generator 108 generates results and this step is carried out by performing a series of consecutive sub-steps: Results formatting (700) and Report creation (702). Briefly, the Results formatting (700) organizes results in the form of Table and Figures. The Report creation (702) creates report, which can be displayed on computer monitor, printed, send over the internet or a telephone line, or send to a wireless phone or computer or tablet, etc.

Different microscope systems or cell visualization method can be designed for use according to the present invention. The following description is a non-exclusive example of a suitable microscope system. Preferably, the cells should be kept in condition for optimal cell viability and uncorrupted cell division. The microscope system should facilitate tracking of large numbers of individual cells. In some embodiments, different subsets of cells are imaged in parallel under the same time frame and conditions. Image quality and sampling frequency should be of sufficient quality to allow identification of detailed cell features required for automated tracking of cell division events and cell viability. Differential Interference Contrast (DIC) with near infrared (NIR) light (>700 nm) provides the best prophylactic lighting conditions and required resolution for continuous cell imaging. DIC imaging provides sufficient detail to track cell behavior while providing high contrast data for computer analysis. The microscope system uses Back thinned Electron Multiplication Cameras (BT EMCCD). An example microscope system can use a high resolution nonimmersion objective which gives enough working distance to freely move between different sample populations and also eliminates the concern of focal drift and cell viability due to localized temperature fluctuations. A magnification system compensates for a small loss in resolution. A heated housing area for the cells is highly preferred, and such housing may accommodate triple gas or single gas perfusion and humidity control for a multichambered cell well system designed around optic grade glass.

Different tracking software routines can be designed to automate the tracking portion of the process. The following are example routines for carrying out the tracking and classifying (identification) of the cells and cell events. The auto-cell tracking system employs gravity center tracking and non-fluorescence image processing and can be summarized as follows: 1. Apply Gaussian bluer to remove noise. 2. Apply threshold and then paint the area above the threshold (bright parts of cells are extracted). 3. Carry out connectivity analysis. 4. Identify the connective pixels of the target cell. 5. Determine the gravity center of the connected pixels. 6. Load next image. 7. Repeat step 1-5. Gravity center indicates the position of the target cell. Thus this software is capable to track cells. If one neighboring mitotic cell moves close to the target cell, two connective pixels merge. Thus, this software is no longer able to segment two cells. Because the gravity center of the target cell shifts due to the merging, when this program detects the shift, it terminates cell tracking. The cell division identification works as follows: 1. Up to the connectivity analysis process, the same approach as described above is used. 2. Draw vectors around the connective pixels. 3. Create vector pattern library (the library contains about 100 repetitive patterns). 4. Compare vector pattern of the target cell with the patterns in the library. If the pattern of target cell matches with any one in the library, the cell is considered to enter mitosis. 5. Determine the connected pixel number of the mitotic cell and its gravity center. 6. Load next image. 7. Check the gravity center of the mitotic cell and the number of pixels of the connective pixels. If the pixel number is significantly reduced (~40-60%), the software recognizes that cell division occurs. 8. Look for the nearest connected pixels to find its sibling.

To track the movement of mitotic cells close to target cells, the steps of the analysis software are the following: 1. In order to recognize an approaching cell, gravity center of all connective pixels in the image will be determined. 2. If the approaching cell moves on the target cell, connective pixels of the approaching cell will be merged with the connective pixels of target one, implying that one gravity center will disappear. This is the signal to start the handling of the "moving of mitotic cells close to target cell" situation. 3. The mitotic cell is usually brighter than the target cell, as it reflects more light. Position of the mitotic cell is predicted by carrying out connectivity analysis of brighter pixels. 4. Software focuses on connective pixels of both brighter and remaining pixels (determines gravity center of each ones). 5. When the connective pixel of brighter pixels starts to move, the software tries to segment the target cell. This can be done by applying several different thresholds to the image and carrying out connectivity analysis. If target cells can be segmented, the process comes back to normal tracking.

For cell division, the software checks the images as follows. 1. When the target cell enters mitosis, determine the gravity center of connective pixel of the cell and, if the software failed to detect cell division, load the next image. 2.

Because divided cells are created near the position of its mitotic cell, software searches connectivity pixels around that position and, if software finds a connectivity pixels, examine whether it belongs to non-target cells. 3. If it does not belong to non-target cells, the connectivity pixels will be marked as a candidate for progeny of the mitotic cell. 4. Load next image and repeat step 2-3. Continue this process until two (dipolar division) or three (tripolar division) connective pixels are identified.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The invention is further illustrated by the following examples, which should not be construed as further limiting.

EXAMPLES

Example 1

Control Analysis

In this study, one of the frequently used carcinogens/mutagens, N-methyl-N'-nitroso-N-nitrosoguanidine (MNNG), an anti-cancer compound and topoisomerase inhibitor, camptothecin (CPT), other carcinogens, formaldehyde, arsenic acid and cadmium, and non-carcinogens, acetaminophen and ibuprofen, were used.

HeLa S3 and MCF10A cells were purchased from ATCC. A549-luc-C8 Bioware® cells were obtained from Caliper LifeSciences.

A Quorum WaveFX Spinning Disc Confocal System™ (Quorum Technologies Inc., Canada) with a Leica microscope controlled by Volocity™ v4.0 was employed for long-term live cell imaging. Differential interference contrast (DIC) images were taken through HCX PL APO™ 40× oil objectives (NA=1.25) by using a Halogen lamp as a light source (UV light from the lamp was removed nearly to 100% using DIC prism filters). Cells grown on a coverglass Lab-Tek™ 8 well chamber were placed on the microscope stage and were cultured using an environmental chamber at 37° C. with 7.5% humidified $CO_2$ (Pathology Devices Inc, Md.). XY positions of field of views (FOVs) were then registered using Volocity v4.0. DIC images were captured every 10 min (34 msec exposure) from the +10 to the −10 μm position relative to the focal plan with 1 μm increment using a piezo focus drive.

Cells grown on a coverglass Lab-Tek™ 8 well chamber were exposed to various concentrations of chemical compounds for 15 to 30 min in a serum-free medium.

In order to carry out long-term cell imaging that would cover more than 100 cell lineages through the entire observation period, we selected an area that contained the appropriate number of cells. In the case of HeLa cells an area of about 70% surface area occupancy was typically selected. Because A549 and MCF10A are highly mobile, we started our observation with an occupancy close to 90~100%.

Volocity™ image sequence files (multi-layer TIFF) were split into single-layer TIFF files. Then, the optimal focal planes for each FOV were selected. By employing Quick-Time player Pro, movies were made. If image quality was not optimal for cell tracking, contrast of TIFF images were adjusted using the batch processing function of Photoshop™ v7.0.

Panorama views of T=1 were prepared and cell lineage numbers were assigned to cells in selected area. After assigning cell lineage numbers, time point that distinctive events occur were determined.

Time points for events determined during cell tracking were entered into a cell lineage database (Database). Cell numbers were assigned upon entering time point data into the Database.

siRNA treatment was carried out after placing a coverglass Lab-Tek™ 8 well chamber on the microscope stage. Scramble siRNA as control (2 μg, medium length, Invitrogen) or p53 siRNA (2 μg, New England Bio Labs) were mixed with 8 μl EC and 0.4 ml enhancer reagents (Qiagen) for 5 min. Then 1 μl effectante (Qiagen) was added to the mix followed, after 10 min of incubation, by 120 μl of culture medium. To each well, 118 μl of mixture was added and cells were cultured for 24 in the environment chamber on the microscope. After replacing the mixture with complete medium, cells were cultured another 24 hrs and then were exposed to MNNG. Because transfected cells contained lipid vesicles, transfection efficiency was determined through visual examination and efficiency was concluded to be over 99%. Transfection efficiency using Cy3-conjugated siRNA was also 98% and the expression level of p53 detected by anti-p53 antibody (Calbiochem) was reduced to less than 10% of control 48 hrs after transfection.

In FIG. 2, outline of the method is illustrated. The method comprising live cell imaging movies, individual cell tracking, building a Database and data analysis. By using a 8 well-chambered coverglass, cells treated with various doses of substances can be monitored simultaneously, allowing real-time cell biological assays to be performed on the microscope stage with their appropriate control (FIGS. 2B and C). Cells were concurrently visualized using DIC imaging technique for 100~160 hrs to obtain accurate cell profiling data, which allowed to determine the frequency of occurring distinctive cellular events (example images of dipolar cell division DD, tripolar cell division TD, tetrapolar cell division QD, and incomplete and impaired cell division IP are shown in FIG. 8, of cell fusion CF are in FIG. 9 and of cell death CD are in FIG. 10). In a typical experiment, cell monitoring was carried out using 120 panoramic FOV for 160 hrs, creating 2,268,000 image files, which were eventually converted into 120 independent imaging movies.

Then, a panorama view of every well was created in order to assign a unique cell lineage number to each cell that was followed by individual cell tracking (FIG. 3A-F). Tracking data, such as time points for the occurrence of distinctive cellular events were entered into the Database. Cell lineage maps were created and, upon creation of the maps, unique identification numbers were assigned to each progeny cell (FIG. 4).

Reproducibility of the analysis was examined by carrying out three independent control experiments by tracking of 1000 to 2000 cells derived from 100 to 200 progenitors. The growth rate variation was within the standard error of about 10% (FIG. 5). Doubling time variation was shown in FIG. 6 by histogram and standard errors of each column were also within 10%, suggesting that this method allows obtaining highly reproducible results by tracking about 1000 to 2000 progenies.

Example 2

Determination of Cell Quality Index (CQI)

Distinct from end point assays, analysis of the data obtained with this real-time based cell biological method requires a new approach to quantitatively represent the characteristics of cell lineages and cell populations by taking into account on-going distinctive cellular events. Thus, we created Cell quality index (CQI), which was calculated for each cell lineage, and used to find the characteristics or to evaluate the quality of the cell population by determining the average CQI of cell lineages within the population. Two formulas were used.

The first formula is: CQI=[$A$×number of dipolar cell division (DD)]+[$B$×number of tripolar cell division (TD)]+[$C$×number of quadpolar cell division (QD)]+[$D$×number of hexapolar cell division (HD)]+[$E$×number of fusion (CF)]+[$F$×number of cell death (CD)]+[$G$×number of incomplete and number of partial cell division (IP)]+[$H$×number of cells showing cell shape alteration (CSA)]+[$I$×number of cells showing nuclear shape alteration (NSA)]+[$J$×number of cells showing inner cellular material accumulation (IA)], +[$K$×number of cells showing cell enlargement (CE)]+[$L$×number of cells showing engulfing (EG)]+[$M$+number of cells showing hyper-mobilization (HEM)]+[$N$×number of cells showing hypo-mobilization (HPM)]+[$O$×number of cells showing prolonged doubling time (PD)]+[$P$×number of cells showing shortened doubling time (SD)]. (Formula 1)

Figure 7A:
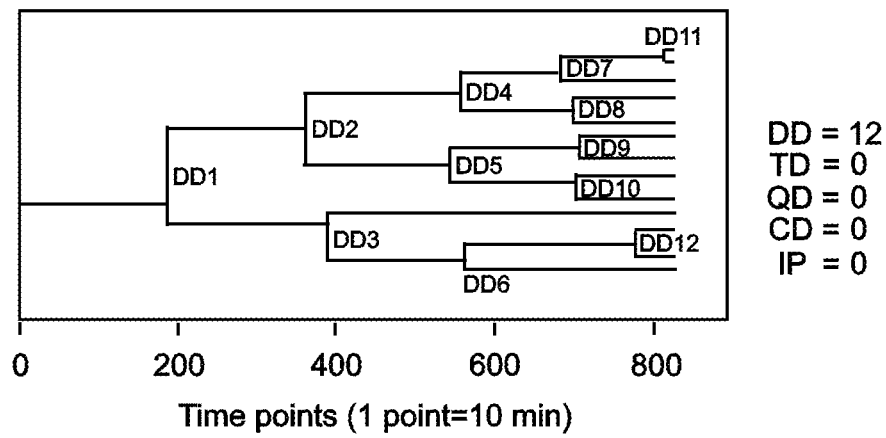
FIG. 7 includes FIGS. 7A and 7B, which are illustrating examples of the data utilized to calculate Cell quality index (CQI) by using Formula 1 with constants, A=1, B=0.8, C=0.8, D=-0.1, E=-0.1, F=0, G=0, H=0, I=0, J=0, K=0, M=0, N=0 O=0 and P=0. Progenies of cell lineage shown in FIG. 7A entered DD 12 times and zero time for TD, QD, CD, and IP. CQI was calculated as 1×(Constant A)×12 DD=12. Some progenies of the cell lineage shown in FIG. 7B entered DD 10 times, TD 2 times and CD 6 times. CQI was calculated as 1×(Constant A)×10 DD+0.8 (Constant B)×2 TD−0.1 (Constant E)×6 CD=10.9.
Figure 7B:
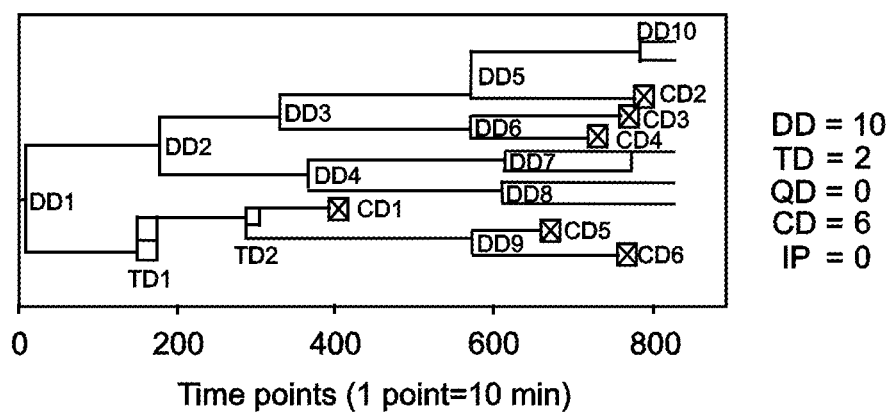

Constants, A to P, are real number and typically −1.000 to +1.000 were used. In a simple case with constants, A=1, B=0, C=0, D=0, E=0, F=0, G=0, H=0, I=0, J=0, K=0, M=0, N=0, O=0 and P=0, the only the frequency of DD is taken into account on the CQI calculation. For example, CQI of the cell lineage showing in FIG. 7A was 12 (DD occurs 12 times), which reflected the growth ability of this cell lineage. Instead of constant A, if constant E is 1, the calculated CQI can be used to identify cell lineages, which enter CD more frequently than control cell lineages. In many cases, however, various distinctive events occurred in a same cell lineage, as shown in FIG. 7B. In this case, CQI was calculated as 10.9=1×10 DD+0.8×2 TD−0.1×6 CD. We used 0.8 for the constant of TD (constant B) by considering the fact that TD is an impaired cell division, but it still contributes to the production of progenies. Because a cell, which enters CD, cannot produce any progeny, −0.1 was assigned to the constant for CD (constant E). In this study, we used A=1, B=0.8, C=0.8, D=0.8, E=−0.1, F=0, G=0, H=0, I−0, J=0, K=0, M=0, N=0, O=0 and P=0 in order to evaluate viability of cell lineage and cell population by taking into account the occurrence/frequency of TD, HD, QD and CD.

The second formula is: CQI=([$B$×number of tripolar cell division (TD)]+[$C$×number of quadpolar cell division (QD)]+[$D$×number of hexapolar cell division (HD)]+[$E$×number of fusion (CF)]+[$F$×number of cell death (CD)]+[$G$×number of incomplete and number of partial cell division (IP)]+[$H$×number of cells showing cell shape alteration (CSA)]+[$I$×number of cells showing nuclear shape alteration (NSA)]+[$J$×number of cells showing inner cellular material accumulation (IA)], +[$K$×number of cells showing cell enlargement (CE)]+[$L$×number of cells showing engulfing (EG)]+[$M$+number of cells showing hyper-mobilization (HEM)]+[$N$×number of cells showing hypo-mobilization (HPM)]+[$O$×number of cells showing prolonged doubling time (PD)]+[$P$×number of cells showing shortened doubling time (SD)/([$A$×number of dipolar cell division (DD)]+[$B$×number of tripolar cell division (TD)]+[$C$×number of quadpolar cell division (QD)]+[$D$×number of hexapolar cell division (HD)]). (Formula 2)

This formula, which is a variation of Formula 1, calculates the frequency of distinctive events (other than DD was divided by DD+TD+QD+HD). If all constants are 1, calculated CQI×100 is equivalent to the % of certain distinctive events relative to total cell division. Similar to the case of Formula 1, various combination of constants can be used, while we used A=1, B=1, C=1, D=1, E=1 and G=1, and 0 for others with Formula 2 in this study.

It should be noted, by applying this concept, various variations of formulas with variety of set of constants can be created in order to quantitatively evaluate the characteristics of cell lineages and cell population.

Example 3

Cell Quality Tests

HeLa cells are derived from cervical tissue and are frequently used for studies on DNA damage responses or cell division. It has been casually known that the cells are a highly heterogeneous cell population, although such heterogeneity has not been previously analyzed in a quantitative manner by employing a long term live cell imaging. Thus, the individual tracking of 100 to 200 progenitors was carried out in order to test whether the method can quantitatively determine the quality of cell population by revealing such heterogeneity. The results indicate that 44 out of the 114 progenitors (T=1) spontaneously died, while 5 progenitors were capable to expand their progenies for up to more than 21 progenies, undergoing at least 4 cell divisions. The remaining 65 progenitors survived, but proliferated less than the above 4 progenitors. In addition, HeLa cells frequently entered cell fusion (CF) and multipolar division (MD). In some cases, poorly growing, pro-CF and pro-MD lineages were created from well-growing cell lineages. These results demonstrated that these well-growing stem cell-like cell populations contribute to maintain the overall growth rate of the HeLa cell population. The data also suggest that the creation of some progenies, which entered distinctive cellular events, e.g. CF, MD are involved in the formation of heterogeneous cell population. In addition, similar cell lineages were quantitatively identified within A549 lung carcinoma, MCF10A non-transformed breast epithelial and primary lung epithelial cell population by this method. Based on these results, we concluded that this method has capacity to precisely determine the quality of a given cell population.

Example 4

Dosage, Carcinogen and Anti-Cancer Drug

Figure 5A:
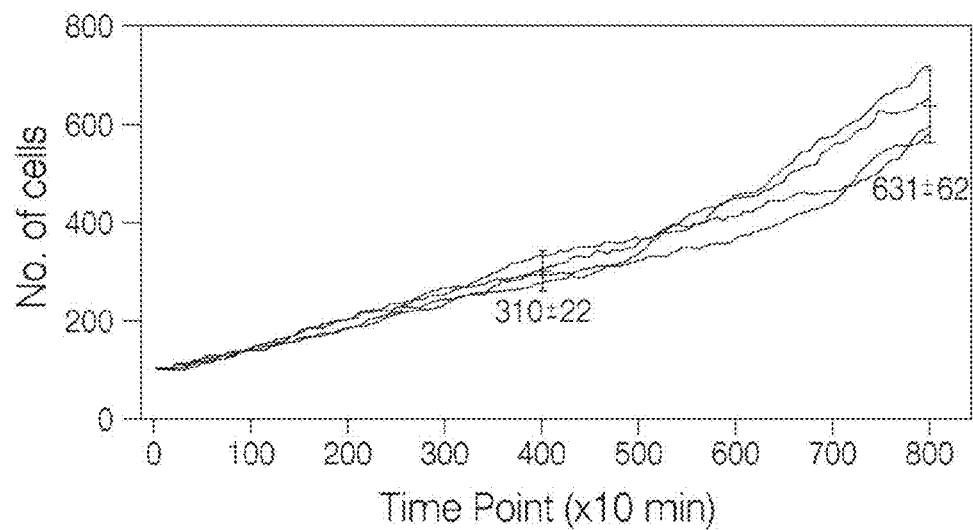
FIG. 5 is a graph of the cell growth curve determined based on cell lineage data and includes FIG. 5A and FIG. 5B, wherein Non-treated cells (FIG. 5A) and cells exposed to non-cytotoxic dose of methylnitronitrosoguanidine (MNNG, 1 μM) (FIG. 5B) were used for individual cell tracking, after entering data into a cell lineage database, the number of cells in every 10 min was calculated. Means and standard deviations are shown.
Figure 5B:
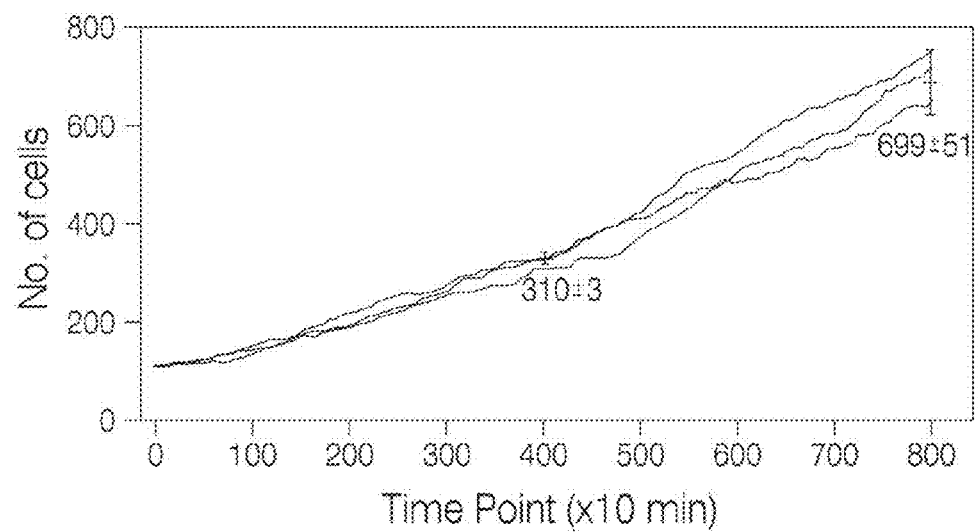
Figure 6A:
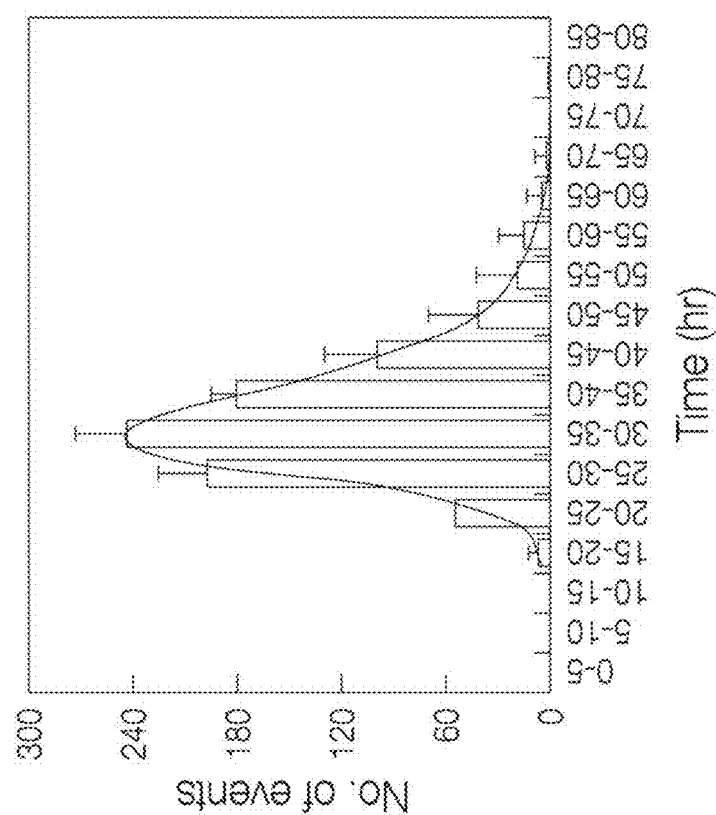
FIG. 6 is a graph of the doubling time determined based on cell lineage data and includes FIG. 6A and FIG. 6B, wherein by employing database, doubling time of non-treated cells (FIG. 6A) and cells exposed to 1 μm MNNG (FIG. 6B) was determined, standard deviations are shown.
Figure 6B:
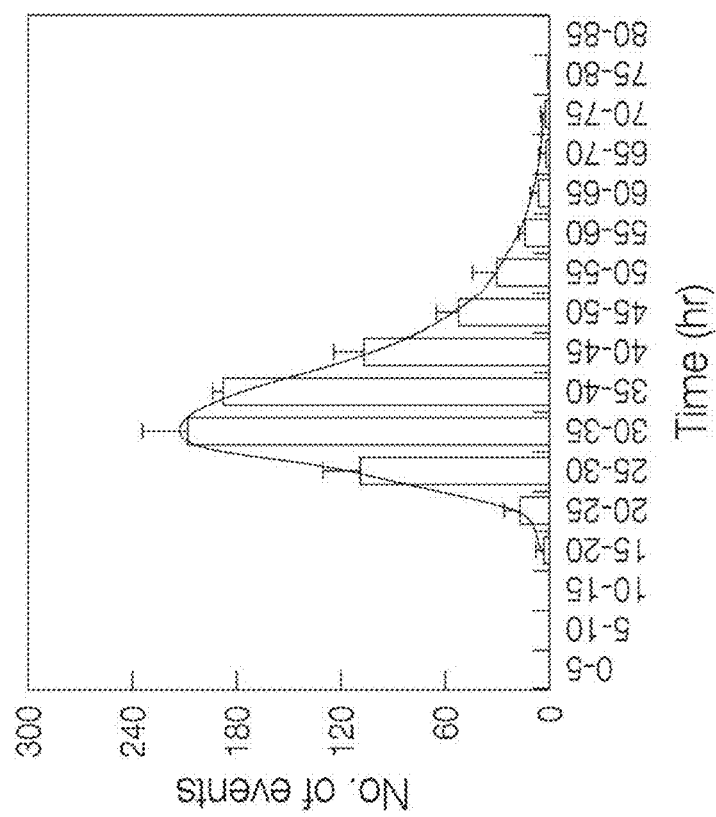

Because the method allows carrying out dose response experiments on microscope, the sub- and non-cytotoxic doses of the chemicals used in this study was defined by exposing cells to different dose of test compounds and carrying out concurrently monitoring these exposed and non-exposed cells. In the case of camptothecin (CPT), exposure of HeLa cells to 0.25 μM for 30 min resulted in 95% cell survival when a classical clonogenic end-point assay was used. On the other hand, when the viability of HeLa cells to the treatment was evaluated based on average CQI (Formula 1), it was calculated to be 60% of control (Table 1) due to a suppression of cell growth, which cannot be easily detected by the existing or conventional clonogenic assays. This dose was defined as a sub-cytotoxic dose, a dose, which does not induce cell death (CD) but still has a negative effect on cell growth. Similarly, a dose of 2 μM N-methyl-N'-nitroso-N-nitrosoguanidine (MNNG) was also defined as a sub-cytotoxic dose due to its suppressive activity on cell growth. In contrast, a dose of 0.1

μM CPT and 1 μM MNNG were defined as non-cytotoxic doses, since these doses caused neither CD induction nor cell growth suppression (FIG. 5A compared to FIG. 5B). Non-cytotoxic doses of formaldehyde, arsenic acid and cadmium were also determined by this method and they were 0.002 to 0.18 μM, 0.009 to 0.7 μM and 0.004 to 0.3 μM, respectively. These results indicate that this method allow to carry out dose-response study within low dose ranges. In the low dose-ranges, induced cellular responses only in limited number of cells were extremely difficult to be detected by other existing methods.

In order to further investigate responses of HeLa cells to MNNG exposure, lower and non-cytotoxic dose of MNNG were then employed. The Average CQI of HeLa cells exposed to 1 μM MNNG was 117% (Table 1) due to the absence of cell growth suppression and CD induction. Despite the absence of cytotoxicity, the multipolar cell division (MD) and cell fusion (CF) of cells exposed to a non-cytotoxic dose of MNNG were about 2 fold higher than control (Table 2), suggesting that MD and CF frequencies were unexpectedly increased by exposure to a non-cytotoxic dose of MNNG. Furthermore, within cell populations exposed to non-cytotoxic doses of formaldehyde, arsenic acid and cadmium, cells that entered MD were more frequently found than control cell populations. In contrast, such increase in the frequency of MD was not observed when cells were exposed to well-established non-apparent human carcinogens, acetaminophen and ibuprofen. These results suggest that carcinogenic potential of substances to humans can be assessed by determining the total MD of cells exposed to their non-cytotoxic doses.

When cells were exposed to 0.25 μM of an anti-cancer compound, CPT, average CQI (Formula 1) was reduced to 60% of control (Table 1) due to cell death induction and cell growth suppression. This dose of CPT (0.25 μM) reduced total MD (Table 2) as well. CPT was thus induced an opposite effect to the carcinogens. Thus, results suggest that substances, which have effect to reduce MD and to increase CD as well as to suppress cell growth, in cells exposed to their non- or sub-cytotoxic dose could be a compound that can be used as an anti-cancer drug.

Example 5

Other Type of Cells

Other cells were then employed: p53 proficient epithelial cells derived from lung carcinoma, A549 cells, and breast non-transformed epithelial cells, MCF10A. First, we determined a non-cytotoxic dose of MNNG for these cells. Exposure of A549 cells to 2 μM of MNNG caused a 20% reduction of average CQI, while no such reduction was found after exposure to 1 μM MNNG. We concluded that 2 and 1 μM are sub- and non-cytotoxic doses, respectively. A non-cytotoxic dose of 1.25 μM MNNG was also determined for MCF10A cells. Then, effect of a non-cytotoxic dose of MNNG on these cells was examined. MD found in non-treated A549 cells was significantly less compared to that of HeLa cells, possibly due to the presence of a functional p53. Exposure to both non- and sub cytotoxic doses of MNNG increased MD frequencies in A549 cells. Furthermore, such frequencies were also increased by exposure of MCF10A cells to a non-cytotoxic dose of MNNG, indicating that, even in p53 proficient and non-transformed cells, a non-cytotoxic dose of MNNG increases the risk of cells entering MDs.

The effect of p53 removal on MD was examined, as p53 is known to play a critical role in the maintenance of genomic integrity and acts as a tumor suppressor. After placing A549 or MCF10A cells on the microscope stage, a p53 siRNA treatment was carried out. Then, the effects of p53 removal on MD and CF were analyzed. Interestingly, p53 removal had a slight promoting effect on cell growth. Furthermore, it was found that these cells more frequently entered MD. In addition, CF frequently occurred prior to MD in those cells. Although it is not clear whether CFs and MDs are mechanistically linked, these results suggest that, in the absence of p53, the risk of cells entering MDs is significantly increased.

Table 1 shows average CQI of HeLa cells treated with CPT and MNNG. HeLa cells were exposed to either CPT or MNNG. Cell imaging movies were then created and 120 to 200 progenitor cells were tracked. CQI of each cell lineage was determined by employing constants, A=1, B=0.8, C=0.8, D=−0.1, E=−0.1, F=0, G=0, H=0, I=0, J=0, K=0, M=0, N-0 O=0 and P=0 with the Formula 1 and average CQI of cell lineage within cell population was calculated.

TABLE 1

|  | Non-treated | CPT 0.1 μM | CPT 0.25 μM | CPT 1 μM | MNNG 1 μM | MNNG 2 μM | MNNG 5 μM |
| --- | --- | --- | --- | --- | --- | --- | --- |
| Average CQI | 9.1 ± 1.1 | 9.3 | 6.2 | 1.8 | 11 ± 1.1 | 3.8 | 1.5 |
| % of control | 100 | 102 | 60 | 22 | 117 | 42 | 19 |

Table 2 provides a summary of MD events for HeLa cells. Approximately 120 to 200 progenitor cells were tracked. Data were normalized by 200 progenitors. The legend for Table 2 is as follows: a. Total cell division (DV) is sum number of cell division events; total DV=number of DD+number of TD+number of QD+number of HD, b. Multipolar division (MD) is sum number of MD events; number of TD+number of QD+number of HD, CQI (Formula 2) is calculated by employing constant of A=1, B=1, C=1, D=0, E=0, F=0, G=0, H=0, I=0, J=0, K=0, M=0, N=0 O=0 and P=0 with CQI Formula 2, p values were calculated by comparison to the events occurring in non-treated cells, **: P<0.1.

TABLE 2

|  | Non-treated | CPT 0.25 μM | MNNG 1 μM |
| --- | --- | --- | --- |
| DD | 1647 ± 1.1 | 1059 ± 95 | 1839 ± 210 |
| TD | 42.5 ± 7.8 | 23.0 ± 3.2 | 76.0 ± 9.2 |
| QD | 8.0 ± 4.3 | 4.0 ± 1.2 | 12.2 ± 9.2 |
| Total DV[a] | 1716 ± 220 | 1086 ± 9.7 | 1983 ± 199 |
| MD[b] | 53.2 ± 8.8 | 27.0 ± 4.5** | 88.3 ± 17.5** |
| CQI (Formula 2) | 0.031 | 0.026 | 0.045 |

As shown in the present examples, the invention allows quantitative determination of quality or condition of a cell population (Example 2 and 3). By exposing cells to a test substance, alteration of the quality or the condition of cell population could occur in either entire a cell population or some progenies of one or more cell lineages in a given plurality of cells. By detecting such alteration, the invention also allows to identify potential carcinogenic substances and/or anti-cancer substance (Example 4).

Headings are included herein for reference and to aid in locating certain sections. These headings are not intended to limit the scope of the concepts described therein under, and these concepts may have applicability in other sections throughout the entire specification. Thus, the present invention is not intended to be limited to the embodiments shown herein but is to be accorded the widest scope consistent with the principles and novel features disclosed herein.

As used herein and in the appended claims, the singular forms "a", "an", and "the" include plural referents unless the context clearly indicates otherwise. Thus, for example, reference to "a compound" includes one or more of such compounds, and reference to "the method" includes reference to equivalent steps and methods known to those of ordinary skill in the art that could be modified or substituted for the methods described herein.

Unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

The invention claimed is:

1. A method for calculating a minimal carcinogenic dose of a carcinogenic compound on a population of cells, comprising:
    culturing a population of live mammalian cells;
    treating the population of mammalian cells with a dose of a carcinogenic compound by treating a first portion of the population of mammalian cells with the carcinogenic compound at a first dose, and treating a second portion of the population of mammalian cells with the carcinogenic compound at a second dose;
    tracking individual cells within said population of cells for measuring by non-fluorescent microscopic observation, and imaging or tracking an occurrence of one or more distinctive cellular events in said population of cells, wherein said one or more distinctive cellular events is selected from the group consisting of:
    dipolar division, tripolar division, quadripolar division, hexapolar division, cell fusion, incomplete or partial division, cell shape alteration, nuclear shape alteration, inner cellular material accumulation, cell enlargement, engulfing, hyper-mobilization, hypo-mobilization, prolonged doubling time, shortened doubling time, and combinations thereof;
    calculating a first frequency of distinctive cellular events for the first portion of treated population of mammalian cells, and calculating a second frequency of distinctive cellular events for the second portion of the treated population of mammalian cells, and
    calculating a minimal carcinogenic dose of the carcinogenic compound based on a comparison between the first frequency and the second frequency, wherein the minimal carcinogenic dose does not reduce cell viability.

2. The method of claim 1, wherein said population of cells is a population of therapeutic mammalian cells adapted to be transferred to a mammalian subject.

3. The method of claim 1, further comprising calculating a control frequency of distinctive cellular events for an untreated population of mammalian cells, and comparing the frequency calculated from the treated population of mammalian cells with the control frequency to determine the minimal carcinogenic dose of the carcinogenic compound.

4. The method of claim 1, comprising calculating a cell quality index for said population of cells,
    wherein the cell quality index (CQI) is calculated from the following formula:

$$CQI=[A\times\text{number of dipolar cell division (DD)}]+[B\times\text{number of tripolar cell division (TD)}]+[C\times\text{number of quadpolar cell division (QD)}]+[D\times\text{number of hexapolar cell division (HD)}]+[E\times\text{number of fusion (CF)}]+[F\times\text{number of cell death (CD)}]+[G\times\text{number of incomplete and number of partial cell division IP}]+[H\times\text{number of cells showing cell shape alteration (CSA)}]+[I\times\text{number of cells showing nuclear shape alteration (NSA)}]+[J\times\text{number of cells showing inner cellular material accumulation (IA)}],+[K\times\text{number of cells showing cell enlargement (CE)}]+[L\times\text{number of cells showing engulfing (EG)}]+[M\times\text{number of cells showing hyper-mobilization (HEM)}]+[N\times\text{number of cells showing hypo-mobilization (HPM)}]+]O\times\text{number of cells showing prolonged doubling time (PD)}]+[P\times\text{number of cells showing shortened doubling time (SD)}],$$

wherein constants A to P are real numbers between, and including, −1.000 to +1.000,
    wherein constants A to P are not zero,
    wherein the calculation of the minimal carcinogenic dose is based on the cell quality index.

5. The method of claim 1, wherein the treating the population of mammalian cells with a dose of a carcinogenic compound includes treating a plurality of portion of the population of mammalian cells with the carcinogenic compound at a plurality of dose levels,
    wherein the method further includes calculating a frequency of distinctive cellular events for each of the plurality of portions of the population of mammalian cells,
    wherein calculating the minimal carcinogenic dose is based on a comparison between the plurality of frequencies.

6. The method of claim 1 wherein the population of mammalian cells is treated with the carcinogenic compound for at least 24 hours, and wherein the population of mammalian cells is tracked over a time between, and including, 100 to 160 hours.

7. The method of claim 1 further comprising generating a cell quality index (CQI), wherein the cell quality index is calculated from the following formula:

$$CQI=[A\times\text{number of dipolar cell division (DD)}]+[B\times\text{number of tripolar cell division (TD)}]+[C\times\text{number of quadpolar cell division (QD)}]+[D\times\text{number of hexapolar cell division (HD)}]+[E\times\text{number of fusion (CF)}]+[F\times\text{number of cell death (CD)}]+[G\times\text{number of incomplete and number of partial cell division (IP)}],$$

wherein constants A to G are 1,
    wherein the calculation of the minimal carcinogenic dose is based on the cell quality index.

8. The method of claim 1, wherein tracking individual cells within said population of cells for measuring occurrence of one or more distinctive cellular events in said population of cells includes the use of a non-fluorescent microscopic observation.

9. The method of claim 1, wherein tracking individual cells within said population of cells for measuring occurrence of one or more distinctive cellular events in said population of cells includes the use of a cell-lineage tracking and imaging device.

\* \* \* \* \*